United States Patent
Karin et al.

(10) Patent No.: US 7,189,832 B1
(45) Date of Patent: Mar. 13, 2007

(54) GAMMA SUBUNIT OF CYTOKINE RESPONSIVE IκB-ALPHA KINASE COMPLEX AND METHODS OF USING SAME

(75) Inventors: Michael Karin, La Jolla, CA (US); David M. Rothwarf, La Jolla, CA (US); Ebrahim Zandi, Duarte, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/377,795

(22) Filed: Aug. 20, 1999

Related U.S. Application Data

(60) Provisional application No. 60/097,418, filed on Aug. 20, 1998.

(51) Int. Cl.
  C07H 21/04 (2006.01)
  C07K 14/00 (2006.01)
(52) U.S. Cl. ............... 536/23.1; 536/24.5; 530/350
(58) Field of Classification Search .............. 435/6, 435/366, 375, 91.1, 183; 536/23.1, 24.3, 536/24.5; 514/44; 530/350
  See application file for complete search history.

(56) References Cited

OTHER PUBLICATIONS

Accession, Image: 761011 5', mRNA sequence Apr. 23, 1997 AA387553.*
Accession, Image: 741357 3', mRNA sequence Nov. 9, 1997 AA402683.*
Shoji Yamaoka et al., Complementation Cloning of Nemo, a Component of the IkB Kinase Complex Essential for NF-kB Activation. Cell, vol. 93, pp. 1231-1240 Jun. 26, 1998.*
GenBank Accession No.: AF074382, 2001.
GenBank Accession No.: R54695, 1995.
GenBank Accession No.: AA133061, 1996.
GenBank Accession No.: AF069542, 1998.
Baeuerle and Baltimore, "NF-κB: ten years after," *Cell* 87(1):13-20.
Baeuerle and Henkel, "Function and activation of NF-κB in the immune system," *Annu. Rev. Immunol.* 12:141-179 (1994).
Barnes and Karin, "Nuclear factor-κB: a pivotal transcription factor in chronic inflammatory diseases," *N. Engl. J. Med.* 336(15):1066-1071 (1997).
DiDonato et al., "A cytokine-resonsive IκB kinase that activates the transcription factor NF-κB," *Nature* 388(6642):548-554 (1997).
DiDonato et al., "Phosphorylation of IκBα precedes but Is not sufficient for its dissociation for NF-κB," *Mol. Cell. Biol.* 15(3):1302-1311 (1995).
Dumont et al., "Cross-talk between steroid and NF-κB: what language?" *TIBS* 23:233-235 (1998).
Karin, "The NF-κB activation pathway: Its regulation and role in inflammation and cell survival," *The Cancer Journal from Scientific American* 4(1):S92-S99 (1998).
Karin and Delhase, "JNK or IKK, AP-1 or NF-κB, which are the targets for MEK kinase 1 action?" *Proc. Natl. Acad. Sci. USA* 95(16):9067-9069 (1998).

(Continued)

*Primary Examiner*—James Schultz
*Assistant Examiner*—Tracy Vivlemore
(74) *Attorney, Agent, or Firm*—Medlen & Carroll LLP

(57) ABSTRACT

The present invention provides a novel essential regulatory subunit of the IκB kinase (IKK) complex, IKK-γ. The isolated IKK-γ subunit of the invention has substantially the same amino acid sequence as SEQ ID NO: 2 shown in FIG. 2.

6 Claims, 8 Drawing Sheets

```
  1 MNRHLWKSQL CEMVQPSGGP AADQDVLGEE SPLGKPAMLH LPSEQGAPET

51 LQRCLEENQE LRDAIRQSNQ ILRERCEELL HFQASQREEK EFLMCKFQEA

101 RKLVERLGLE KLDLKRQKEQ ALREVEHLKR CQQQMAEDKA SVKAQVTSLL

151 GELQESQSRL EAATKECQAL EGRARAASEQ ARQLESEREA LQQQHSVQVD

201 QLRMQGQSVE AALRMERQAA SEEKRKLAQL QVAYHQLFQE YDNHIKSSVV

251 GSERKRGMQL EDLKQQLQQA EEALVAKQEV IDKLKEEAEQ HKIVMETVPV

301 LKAQADIYKA DFQAERQARE KLAEKKELLQ EQLEQLQREY SKLKASCQES

351 ARIEDMRKRH VEVSQAPLPP APAYLSSPLA LPSQRRSPPE EPPDFCCPKC

401 QYQAPDMDTL QIHVMECIE
```

OTHER PUBLICATIONS

Li et al., "The IKKβ subunit of IκB kinase (IKK) is essential for nuclear facotr κB activation and prevention of apoptosis," *J. Exp. Med.* 189(11):1839-1845 (1999).

Ling et al., "NF-κB-inducing kinase activates IKK-α by phosphorylation of Ser-176," *Proc. Natl. Acad. Sci. USA* 95(7):3792-3797 (1998).

May and Ghosh, "Signal transduction through NF-κB," *Immunology Today* 19(2):80-88 (1998).

Mercurio et al., "IKK-1 and IKK-2: cytokine-activated IκB kinases essential for NF-κB activation," *Science* 278(5339):860-866 (1997).

Nakano et al., "Differential regulation of IκB kinase α and β and by two upstream kinases, NF-κB-inducing kinase and mitogen-activated protein kinase/ERK kinase kinase-1," *Proc. Natl. Acad. Sci. USA* 95(7):3537-3542 (1998).

Régnier et al., "Identification and characterization of an IκB kinase," *Cell* 90(2):373-383 (1997).

Rothwarf et al., "IKK-γ is an essential regulatory subunit of the IκB kinase complex," *Nature* 395:297-300 (1998).

Sha, "Regulation of immune reponses by NF-κB/Rel transcription factors," *J. Exp. Med.* 187(2):143-146 (1998).

Verma et al., "Rel/NF-κB/IκB family: intimate tales of association and dissociation," *Genes Dev.* 9(22):2723-2735 (1995).

Woronicz et al., "IκB kinase-β; NF-κB activation and complex formation with IκB kinaseα and NIK," *Science* 278(5339):866-869 (1997).

Yamaoka et al., "Complementation cloning of NEMO, a component of the IκB kinase complex essential for NF-κB activation," *Cell* 93:1231-1240 (1998).

Zandi et al., "Direct phosphorylation of IκB by IKKα and IKKβ: discrimination between free and NF-κB-bound substrate," *Science* 281(5381):1360-1363 (1998).

Zandi et al., "The IκB kinase complex (IKK) contains two kinase subunits, IKKα and IKKβ, necessary for IκB phosphorylation and NFκB activation," *Cell* 91(2):243-252 (1997).

\* cited by examiner

```
   1 ggcacgagca tggcccttgt gatccaggtg gggaaactaa ggcccagaga agtgaggacc
  61 ccgcagacta tcaatcccag tctcttcccc tcactccctg tgaagctctc cagcatcatc
 121 gaggtcccat cagcccttgc cctgttggat gaataggcac ctctggaaga gccaactgtg
 181 tgagatggtg cagcccagtg gtggcccggc agcagatcag gacgtactgg gcgaagagtc
 241 tcctctgggg aagccagcca tgctgcacct gccttcagaa cagggcgctc ctgagaccct
 301 ccagcgctgc ctggaggaga atcaagagct ccgagatgcc atccggcaga gcaaccagat
 361 tctgcgggag cgctgcgagg agcttctgca tttccaagcc agccagaggg aggagaagga
 421 gttcctcatg tgcaagttcc aggaggccag gaaactggtg gagagactcg gcctggagaa
 481 gctcgatctg aagaggcaga aggagcaggc tctgcgggag gtggagcacc tgaagagatg
 541 ccagcagcag atggctgagg acaaggcctc tgtgaaagcc caggtgacgt ccttgctcgg
 601 ggagctgcag gagagccaga gtcgcttgga ggctgccact aaggaatgcc aggctctgga
 661 gggtcgggcc cgggcggcca gcgagcaggc gcggcagctg gagagtgagc gcgaggcgct
 721 gcagcagcag cacagcgtgc aggtggacca gctgcgcatg cagggccaga gcgtggaggc
 781 cgcgctccgc atggagcgcc aggccgcctc ggaggagaag aggaagctgg cccagttgca
 841 ggtggcctat caccagctct tccaagaata cgacaaccac atcaagagca gcgtggtggg
 901 cagtgagcgg aagcgaggaa tgcagctgga agatctcaaa cagcagctcc agcaggccga
 961 ggaggccctg gtggccaaac aggaggtgat cgataagctg aaggaggagg ccgagcagca
1021 caagattgtg atggagaccg ttccggtgct gaaggcccag gcggatatct acaaggcgga
1081 cttccaggct gagaggcagg cccgggagaa gctggccgag aagaaggagc tcctgcagga
1141 gcagctggag cagctgcaga gggagtacag caaactgaag gccagctgtc aggagtcggc
1201 caggatcgag gacatgagga gcggcatgt cgaggtctcc caggccccct tgccccccgc
1261 ccctgcctac ctctcctctc cctggccct gccagccag aggaggagcc ccccgagga
1321 gccacctgac ttctgctgtc caagtgcca gtatcaggcc cctgatatgg acaccctgca
1381 gatacatgtc atggagtgca ttgagtaggg ccggccagtg caaggccact gcctgcccga
1441 ggacgtgccc gggaccgtgc agtctgcgct ttcctctccc gcctgcctag cccaggatga
1501 agggctgggt ggccacaact gggatgccac ctggagcccc acccaggagc tggccgcggc
1561 accttacgct tcagctgttg atccgctggt cccctctttt ggggtagatg cggcccgat
1621 caggcctgac tcgctgctct ttttgttccc ttctgtctgc tcgaaccact tgcctcgggc
1681 taatccctcc ctcttcctcc acccggcact ggggaagtca agaatggggc ctggggctct
1741 cagggagaac tgcttcccct ggcagagctg ggtggcagct cttcctccca ccggacaccg
1801 acccgcccgc cgctgtgccc tgggagtgct gccctcttac catgcacacg ggtgctctcc
1861 tttgggctg catgctattc cattttgcag ccagaccgat gtgtatttaa ccagtcacta
1921 ttgatggaca tttggggttgt ttcccatctt tttgttacca taaataatgg catagtaaaa
1981 aaaaaaaaaa aaaa
```

Figure 2a b

```
  1 MNRHLWKSQL CEMVQPSGGP AADQDVLGEE SPLGKPAMLH LPSEQGAPET
 51 LQRCLEENQE LRDAIRQSNQ ILRERCEELL HFQASQREEK EFLMCKFQEA
101 RKLVERLGLE KLDLKRQKEQ ALREVEHLKR CQQQMAEDKA SVKAQVTSLL
151 GELQESQSRL EAATKECQAL EGRARAASEQ ARQLESEREA LQQQHSVQVD
201 QLRMQGQSVE AALRMERQAA SBEKRKLAQL QVAYHQLFQE YDNHIKSSVV
251 GSERKRGMQL EDLKQQLQQA EEAIVAKQEV IDKLKEEAEQ HKIVMETVPV
301 LKAQADIYKA DFQAERQARE KLAEKKELLQ EQLEQLQREY SKLKASCQES
351 ARIEDNRKRH VEVSQAPLPP APAYLSSPLA LPSQRRSPPE EPPDFCCPKC
401 QYQAPDMDTL QIHVMECIE
``` c

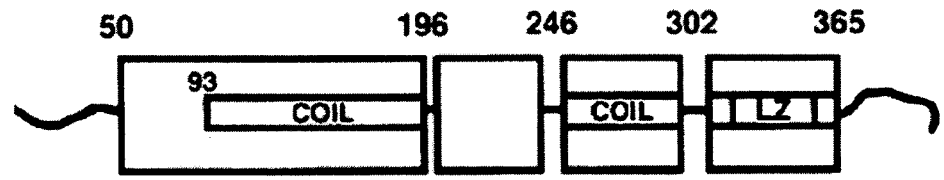

Figure 2 continued

GAMMA SUBUNIT OF CYTOKINE RESPONSIVE IκB-ALPHA KINASE COMPLEX AND METHODS OF USING SAME

This application claims the benefit of U.S. Provisional Application Ser. No. 60/097,418, filed Aug. 20, 1998, and which is incorporated herein by reference.

This invention was made with government support under grant number R01AI43477 awarded by the National Institutes of Health. The government has certain rights in the invention.

BACKGROUND OF THE INVENTION

1. Field of the Invention

The present invention relates generally to molecular biology and biochemistry and more specifically to a subunit of a protein kinase, the IκB kinase, which is activated in response to environmental stresses and proinflammatory signals to phosphorylate inhibitors of NF-κB.

2. Background Information

In chronic inflammatory disease including asthma, rheumatoid arthritis, inflammatory bowel disease and psoriasis, cytokines recruit activated immune and inflammatory cells to the site of lesions, thereby amplifying and perpetuating the inflammatory states. Although the causes of chronic inflammatory disease are in large part unknown, both genetic and environmental factors contribute to pathology. Genes such as those for HLA antigens in rheumatoid arthritis and inflammatory bowel disease can determine a patient's susceptibility to the disease and disease severity, and environmental factors can determine its course. Once established, a chronic inflammatory process is virtually impossible to disrupt; there is no curative treatment for any chronic inflammatory disease. Although chronic disease can be suppressed by glucocorticoid or immunosuppressive therapy, side effects are associated with prolonged treatment.

A ubiquitous transcription factor, nuclear factor-κB (NF-κB), has been identified as of particular importance in immune and inflammatory responses. NF-κB increases the expression of the genes for many cytokines, enzymes, and adhesion molecules in chronic inflammatory diseases. One gene regulated by NF-κB is the gene for inducible nitric oxide synthase, the expression of which is increased in airway epithelial cells and macrophages in patients with asthma; in colonic epithelial cells of patients with the inflammatory bowel disease, ulcerative colitis; and in synovial cells in inflamed joints. The increased expression is reflected by an increased amount of nitric oxide in the exhaled breath of patients with asthma and in the colons of patients with active ulcerative colitis, as well as by elevated urinary nitrite concentrations in patients with rheumatoid arthritis. Cyclooxygenase-2, another inducible enzyme regulated by NF-κB, is responsible for the increased production of prostaglandins and thromboxane in inflammatory diseases.

NF-κB also is involved in expression of adhesion molecules, which recruit inflammatory cells such as neutrophils, eosinophils and T lymphocytes from the circulation to the site of inflammation in all chronic inflammatory diseases. NF-κB regulates the expression of several genes that encode adhesion molecules such as intercellular adhesion molecule 1, vascular cell adhesion molecule 1, and E-selectin.

The production of pro-inflammatory cytokines also can be regulated by NF-κB. Interleukin-1β, TNF-α, interleukin-6, granulocyte-macrophage colony-stimulating factor, and many chemotactic cytokines (chemokines) is increased in patients with asthma, rheumatoid arthritis, psoriasis and inflammatory bowel disease, and all have important roles in the inflammatory process. Interleukin-1β and TNF-α appear to influence severity of disease, possibly by persistent activation of NF-κB.

Thus, the transcription factor NF-κB plays a central role in inflammatory disease. This role is emphasized by the targeted disruption of an inhibitor of NF-κB in mice, which resulted in prolonged activation of NF-κB in response to inflammatory stimuli, and the death of these animals due to widespread inflammation.

Unfortunately, the available therapies for chronic inflammatory diseases such as asthma, rheumatoid arthritis and inflammatory bowel disease are unsatisfactory. Identification of molecules that regulate NF-κB would provide new strategies for screening for anti-inflammatory therapeutics. The present invention satisfies this need by providing the novel IκB kinase subunit, IKK-γ, which is an essential regulatory subunit of the IκB kinase required for NF-κB activation. Related advantages also are provided.

SUMMARY OF THE INVENTION

The present invention provides a novel essential regulatory subunit of the IκB kinase (IKK) complex, IKK-γ. The isolated IKK-γ subunit of the invention has substantially the same amino acid sequence as SEQ ID NO: 2, for example, an amino acid sequence having at least 55% amino acid identity with SEQ ID NO: 2.

Also provided by the invention is an IKK-γ active fragment that has substantially the same amino acid sequence as a portion of the IκB kinase subunit, IKK-γ. An IKK-γ active fragment of the invention can contain, for example, ten, twenty, fifty or more contiguous amino acids of SEQ ID NO: 2 and can have, for example, IKK-β binding activity.

The invention also provides an isolated IKK-γ nucleic acid molecule, which contains a nucleotide sequence encoding substantially the same amino acid sequence as SEQ ID NO: 2. Such an isolated IKK-γ nucleic acid molecule of the invention can have, for example, a nucleotide sequence encoding an amino acid sequence having at least 55% amino acid identity with SEQ ID NO: 2. An isolated IKK-γ nucleic acid molecule of the invention can have a nucleotide sequence encoding SEQ ID NO: 2, for example, nucleotides 149 to 1408 of SEQ ID NO: 1 or the entire sequence of SEQ ID NO: 1.

IKK-γ polynucleotides and antisense polynucleotides also are provided by the invention. The invention provides a polynucleotide containing at least nine contiguous nucleotides of SEQ ID NO: 1. The invention also provides an antisense polynucleotide containing a nucleotide sequence complementary to at least nine contiguous nucleotides of SEQ ID NO: 1.

The present invention also provides a method of identifying an effective agent that modulates the specific association of an IκB kinase γ (IKK-γ) subunit and a second protein. Such agents can represent novel therapeutic agents, such as immunosuppressant, anti-inflammatory or anti-cancer therapeutics. The method includes the steps of contacting the IKK-γ subunit and the second protein with an agent under conditions suitable for the specific association of the IKK-γ subunit and the second protein, and detecting an altered association of the IKK-γ subunit and the second protein in the presence of the agent, where the altered association identifies the agent as an effective agent that modulates the specific association of the IKK-γ subunit and the second protein. In a method of the invention, the contacting can be, for example, in vitro with an isolated IKK-γ subunit. Alternatively, the IKK-γ subunit can be contacted, for example, in a cell such as a mammalian cell or yeast cell in culture. In a method of the invention, an altered association can be detected by a variety of methods, for example, by measuring the transcriptional activity of a reporter gene. In a preferred embodiment, the second protein is IKK-β and an effective agent is identified that modulates the specific association of an IKK-γ subunit and an IKK-β subunit.

Also provided herein is a method of modulating NF-κB activity in a cell by contacting the cell with an effective agent that modulates the specific association of an IKK-γ subunit and a second protein. In a method of the invention, the second protein can be, for example, IKK-β. Methods of modulating NF-κB activity in a cell by introducing into the cell an IKK-γ antisense polynucleotide also are provided. The IKK-γ antisense polynucleotide can be expressed in the cell, for example, in a vector.

BRIEF DESCRIPTION OF THE DRAWINGS

FIG. 2: Primary and secondary structure of IKK-γ. a. The nucleotide sequence of the complete IKK-γ cDNA (SEQ ID NO: 1). The initiator "ATG" is underlined. b. The amino acid sequence of the complete IKK-γ ORF (SEQ ID NO: 2). Peptide sequences obtained by microsequencing are overlined; the leucines of the leucine zipper are indicated by solid dots. c. Secondary structure prediction of IKK-γ. The boxes indicate α-helical regions. "Coil" designates coiled-coil regions, and "LZ" designates leucine zipper motif (which is a coiled-coil). The amino acid positions that mark the approximate boundaries of these motifs are indicated.

DETAILED DESCRIPTION OF THE INVENTION

Proinflammatory cytokines activate the transcription factor NF-κB by stimulating the activity of a protein kinase that phosphorylates IκB, an inhibitor of NF-κB (DiDonato et al., supra, 1997; Mercurio et al., *Science* 278:860–866 (1997); Régnier et al., *Cell* 90:373–383 (1997); Woroniez et al., *Science* 278:866–869 (1997); Zandi et al., *Cell* 91:243–252 (1997)). Phosphorylation occurs at sites that trigger ubiquitination and degradation of IκB, resulting in nuclear translocation of freed NF-κB dimers and activation of target gene transcription (Verma et al., *Genes Dev.* 9:2723–2735 (1995) and Baeuerle and Baltimore, Cell 87:13–20 (1996)) including immunoregulatory target proteins (Woroniez et al., supra, 1997, and Barnes et al., *New Engl. J. Med.* 336:1066–1071 (1997)). Two of the subunits of the large cytokine-responsive IκB kinase complex (IKK) are IKK-α and IKK-β, which are protein kinases whose function is necessary for NF-κB activation by proinflammatory stimuli.

As disclosed herein, the IKK complex is composed of similar amounts of IKK-α, IKK-β and two other polypeptides, whose partial sequences were obtained as set forth in Example I. These polypeptides are differentially processed forms of a third subunit, IKK-γ, having the amino acid sequence SEQ ID NO: 2 (see FIGS. 2a and 2b). Secondary structure prediction algorithms indicate that IKK-γ is predominantly helical with large stretches of coiled-coil structure including a leucine zipper motif as shown in FIG. 2c. Furthermore, the 23 carboxy-terminal residues of IKK-γ share 70% amino acid sequence identity with the carboxy-terminus of FIP-2, including three cysteines and a histidine, encoding a zinc finger motif (Li et al., *Proc. Natl. Acad. Sci. USA* 96:1042–1047 (1999).

Figure 6:
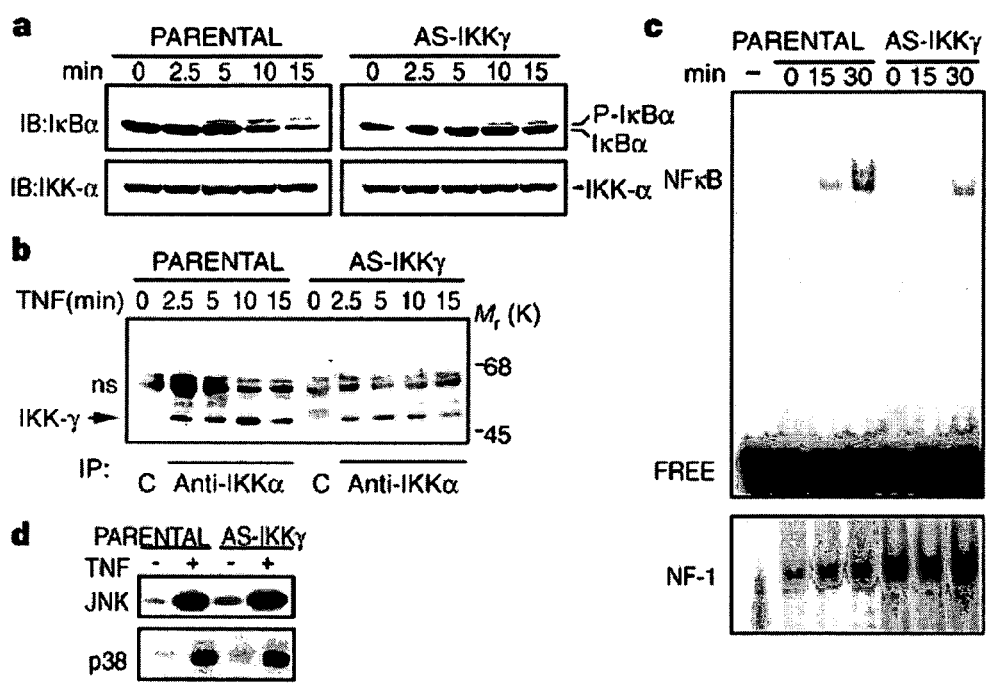
FIG. 6: Reduced IKK-γ expression interferes with IκBα phosphorylation, degradation and NF-κB activation. a. Pools of 293 cells stably transfected with AS-IKK-γ vector and parental mock transfected cells were stimulated with TNF for the indicated times, after which cells were collected and lysed. Lysates were tested by immunoblotting for IκBα degradation and endogenous IKK-α levels. Basal and phosphorylated (P-IκBα) forms are indicated. b. IKK-α immunecomplexes were isolated and immunoblotted with anti-NEMO (anti-IKK-γ) antibody. C, immunoprecipitation with control antibody; ns, nonspecific band. c. Parental cells or pools of 293 cells stably transfected with the AS-IKK-γ vector were incubated with TNF for the indicated times after which nuclear extracts were prepared. The levels of NF-κB and NF-1 DNA binding activities were determined by electrophoretic mobility shift assay as described in DiDonato et al., *Mol. Cell. Biol.* 15:1302–1311 (1995) using probes corresponding to the consensus κB (5'-AGTTGAGGG-GACTTTCCCAGGC-3'; SEQ ID NO: 18) and NF-1 (5'-TTGGATTGAAGCCAATATGATA-3'; SEQ ID NO: 19) sites. d. JNK and p38 activities were determined by immunecomplex kinase assay.

As further disclosed herein, IKK-γ interacts directly with IKK-β in vitro (see FIG. 3d) and can associate with IKK-α to form IKK complexes in IKK-β deficient cells. In addition, the level of TNF-induced IκB kinase activity associated with either IKK-α or IKK-β decreased upon co-transfection with an IKK-γ antisense vector as shown in FIG. 6, indicating that IKK-γ is an essential component of the IKK complex required for its activation and that IKK-γ can function to connect the IKK complex to upstream activators. Thus, the present invention provides a novel essential regulatory subunit of the IκB kinase complex, IKK-γ, and based on this novel regulatory subunit, provides methods of identifying new therapeutic agents that regulate IKK activity and thereby modulate the activity of NF-κB. Such agents can be useful as improved immunosuppressant and anti-inflammatory drugs for treating a variety of disorders involving NF-κB, including autoimmune diseases, asthma, septic shock, arthritis, acquired immune deficiency syndrome (AIDS) and cancer.

NF-κB is a member of the Rel family of transcription factors, which are present in most if not all animal cells (Thanos and Maniatis, *Cell* 80:629–532 (1995)). Rel proteins, which include, for example, RelA (p65), c-Rel, p50, p52 and the *Drosophila* dorsal and Dif gene products, are characterized by region of about 300 amino acids sharing approximately 35% to 61% homology ("Rel homology domain"). The Rel homology domain includes DNA binding and dimerization domains and a nuclear localization signal. Rel proteins are grouped into one of two classes, depending on whether the protein also contains a transcriptional activation domain (Siebenlist et al., *Ann. Rev. Cell Biol.* 10:405–455 (1994)).

Rel proteins can form homodimers or heterodimers, which can activate transcription depending on the presence of a transactivation domain. The most common Rel/NF-κB dimer, which is designated "NF-κB," is a p50/p65 heterodimer that can activate transcription of genes containing the appropriate κB binding sites. p50/p65 NF-κB is present in most cell types and is considered the prototype of the Rel/NF-κB family of transcription factors. Different dimers vary in their binding to different κB elements, kinetics of nuclear translocation and levels of expression in a tissue (Siebenlist et al., supra, 1994). As used herein, the term "Rel/NF-κB" is used to refer generally to the Rel family of transcription factors, and the term "NF-κB" is used to refer specifically to the Rel/NF-κB factor consisting of a p50/p65 heterodimer.

NF-κB originally was identified by its ability to bind a specific DNA sequence present in the immunoglobulin κlight chain gene enhancer, the "κB element" (Sen and Baltimore, *Cell* 46:705–709 (1986)). The κB element has been identified in numerous cellular and viral promoters, including promoters present in human immunodeficiency virus-1 (HIV-1); immunoglobulin superfamily genes such as the MHC class 1 (H-2K) gene; cytokine genes such as the tumor necrosis factor α (TNFα), interleukin-1β (IL-1β), IL-2, IL-6 and the granulocyte-macrophage colony stimulating factor (GM-CSF) gene; chemokine genes such as RANTES and IL-8; and cell adhesion protein genes such as E-selectin. The κB element exhibits dyad symmetry; each half site of the element likely is bound by one subunit of an NF-κB dimer.

In the absence of an appropriate signaling stimulus, a Rel/NF-κB is maintained in the cytoplasm in an inactive form complexed with an IκB protein. Rel/NF-κB transcriptional activity is induced by numerous pathogenic events or stresses, including cytokines, chemokines, viruses and viral products, double stranded RNA, bacteria and bacterial products such as lipopolysaccharide (LPS) and toxic shock syndrome toxin-1, mitogens such as phorbol esters, physical and oxidative stresses, and chemical agents such as okadaic acid and cycloheximide (Thanos and Maniatis, supra, 1995; Siebenlist et al., supra, 1994). Significantly, the expression of genes encoding agents such as TNFα, IL-1, IL-6, interferon-β and various chemokines, which induce NF-κB activity, are, themselves, induced by NF-κB, resulting in amplification of their signal by a positive, self-regulatory loop (Siebenlist et al., supra, 1994). Phorbol esters, which activate T cells, also activate NF-κB and immunosuppressants such as cyclosporin A inhibit activation of T cells through T cell receptor mediated signals (Baldwin, *Ann. Rev. Immunol.* 14:649–681 (1996)).

Regulation of specific genes by NF-κB can require interaction of NF-κB with one or more other DNA binding proteins. For example, expression of E-selectin requires an interaction of NF-κB, the bZIP protein ATF-2 and HMG-I(Y), and expression of the IL-2 receptor α gene requires an interaction of NF-κB, HMG-I(Y) and the ets-like protein, ELF-1 (Baldwin, supra, 1996).

The numerous agents that induce activation of NF-κB likely act through various converging signal transduction pathways, including pathways involving activation of protein kinase C, Raf kinase and tyrosine kinases. The ability of antioxidants to inhibit NF-κB activation by various inducing agents suggests that reactive oxygen species are a converging point of such pathways (Siebenlist et al., supra, 1994).

Upon activation by an appropriate inducing agent, a Rel/NF-κB dimer is translocated into the nucleus, where it can activate gene transcription. The subcellular localization of a Rel/NF-κB is controlled by specific inhibitory proteins ("inhibitors of Rel/NF-κB" or "IκB's"), which noncovalently bind the Rel/NF-κB and mask its nuclear localization signal (NLS), thereby preventing nuclear uptake. Various IκB's, including, for example, IκBα, IκBβ, Bcl-3 and the *Drosophila* cactus gene product, have been identified (Baeuerle and Baltimore, supra, 1996). In addition, Rel precursor proteins, such as p105 and p100, which are precursors of p50 and p52, respectively, function as IκB's (Siebenlist et al., supra, 1994). IκBα and IκBβ are expressed in most cell types and generally bind p65- and c-Rel-containing Rel/NF-κB dimers. Other IκB's appear to be expressed in a tissue specific manner (Thompson et al., *Cell* 80:573–582 (1995)).

IκB proteins are characterized by the presence of 5 to 8 ankyrin repeat domains, each about 30 amino acids, and a C-terminal PEST domain. For example, IκBα contains a 70 amino acid N-terminal domain, a 205 amino acid internal domain containing the ankyrin repeats, and a 42 amino acid C-terminal domain containing the PEST domain (Baldwin, supra, 1996). Although IκB proteins interact through their ankyrin repeats with the Rel homology domain of Rel/NF-κB dimers, binding of particular IκB proteins with particular Rel/NF-κB proteins appears to be relatively specific. For example, IκBα and IκBβ associate primarily with RelA- and c-Rel-containing Rel/NF-κB dimers, thereby blocking their nuclear localization signal. The binding of an IκB to NF-κB also interferes with the ability of NF-κB to bind DNA. However, whereas IκBα is phosphorylated following exposure of cells to tumor necrosis factor (TNF), IL-1, bacterial lipopolysaccharide (LPS) or phorbol esters, IκBβ is phosphorylated in certain cell types only in response to LPS or IL-1 (Baldwin, supra, 1996). However, in other cell types, IκBβ is phosphorylated in response to the same signals that induce IκBα, although with slower kinetics than IκBα (DiDonato et al., *Mol. Cell. Biol.* 16:1295–1304 (1996)).

Formation of a complex between an IκB protein and a Rel protein is due to an interaction of the ankyrin domains with a Rel homology domain (Baeuerle and Baltimore, supra, 1996). Upon exposure to an appropriate stimulus, the IκB portion of the complex is rapidly degraded and the Rel/NF-κB portion becomes free to translocate to the cell nucleus. Thus, activation of a Rel/NF-κB does not require de novo protein synthesis and, therefore, occurs extremely rapidly. Consequently, activation of gene expression due to a Rel/NF-κB can be exceptionally rapid and provides an effective means to respond to an external stimulus. Such a rapid response of Rel/NF-κB transcription factors is particularly important since these factors are involved in the regulation of genes involved in the immune, inflammatory and acute phase responses, including responses to viral and bacterial infections and to various stresses.

Upon exposure of a cell to an appropriate inducing agent, IκBα, for example, is phosphorylated at serine residue 32 (Ser-32) and Ser-36 (Haskill et al., *Cell* 65:1281–1289 (1991)). Phosphorylation of IκBα triggers its rapid ubiquitination, which results in proteasome-mediated degradation of the inhibitor and translocation of active NF-κB to the nucleus (Brown et al., *Science* 267:1485–1488 (1995); Scherer et al., *Proc. Natl. Acad. Sci. USA.* 92:11259–11263 (1995); DiDonato et al., supra, 1996; DiDonato et al., supra, 1995; Baldi et al., *J. Biol. Chem.* 271:376–379 (1996)). The same mechanism also accounts for IκBβ degradation (DiDonato et al., supra, 1996).

Rel/NF-κB activation can be transient or persistent, depending on the inducing agent and the IκB that is phosphorylated. For example, exposure of a cell to particular cytokines induces IκBα phosphorylation and degradation, resulting in NF-κB activation, which induces the expression of various genes, including the gene encoding IκBα. The newly expressed IκBα then binds to NF-κB in the nucleus, resulting in its export to the cytoplasm and inactivation and, therefore, a transient NF-κB mediated response. In comparison, bacterial LPS induces IκBβ phosphorylation, resulting in NF-κB activation. However, the IκBβ gene is not induced by NF-κB and, as a result, activation of NF-κB is more persistent (Thompson et al., supra, 1995).

A large, cytokine-responsive IκB kinase complex (IKK) has been purified, and two of its subunits molecularly cloned (DiDonato et al., supra, 1997; Mercurio et al., supra, 1997; Frishman and Argos, *Protein Eng.* 9:133–142 (1996)). The 85 and 87 kDa catalytic subunits, IKK-α and IKK-β, are protein kinases whose function is necessary for NF-κB activation by proinflammatory stimuli. The α and β subunits contain an N-terminal kinase domain and protein interaction motifs, including a leucine zipper (LZ) and a helix-loop-helix (HLH), at their C-terminal region (DiDonato et al., supra, 1997; Mercurio et al., supra, 1997; Régnier et al., supra, 1997; Woroniez et al., supra, 1997; Zandi et al., supra, 1997). The IKK-α and IKK-β subunits are rapidly activated by tumor necrosis factor (TNF) and interleukin I (IL-1) and are necessary for NF-κB activation (DiDonato et al., supra, 1997; Mercurio et al., supra, 1997; Zandi et al., supra, 1997). IKK activity depends on phosphorylation, as it is inactivated by protein phosphatase 2A (DiDonato et al., supra, 1997), and IKK-α and IKK-β can be phosphorylated and activated by overexpressed NF-κB activating kinase (NIK) (Ling et al., *Proc. Natl. Acad. Sci. USA* 95:2791–2797 (1998)) or MEK kinase 1 (MEKK-1) (Nakano et al., *Proc. Natl. Acad. Sci. USA* 95:3537–3542 (1998) and Karin et al., *Proc. Natl. Acad. Sci. USA* 95:9067–9069 (1998)).

As disclosed herein, the IKK complex was purified to homogeneity from human cell lines using a monoclonal antibody to IKK-α. IKK was composed of similar amounts of IKK-α, IKK-β and two other polypeptides, whose partial sequences were obtained. As disclosed herein, these polypeptides are differentially processed forms of a third subunit, IKK-γ, having the amino acid sequence SEQ ID NO: 2.

Thus, the present invention provides an isolated novel essential regulatory subunit of the IκB kinase (IKK) complex, IKK-γ. The isolated IKK-γ subunit of the invention has substantially the same amino acid sequence as SEQ ID NO: 2, and can have, for example, an amino acid sequence having at least 55% amino acid identity with SEQ ID NO: 2.

As used herein, the term "isolated," when used in reference to an IKK-γ subunit of the invention, means that the subunit is relatively free from contaminating lipids, proteins, nucleic acids or other cellular material normally associated with an IKK-γ subunit in a cell. Thus, an isolated IKK-γ subunit is in a form that is substantially free of the IKK-α and IKK-β subunits that can be associated with IKK-γ in a cell. An isolated IKK-γ subunit can be isolated, for example, by immunoprecipitation using an antibody that binds to an IKK catalytic subunit (IKK-α or IKK-β), followed by SDS-PAGE gel separation, for example (see Example I). In addition, an isolated IKK-γ subunit can be obtained, for example, by expression of a recombinant nucleic acid molecule such as SEQ ID NO: 1 (see Example II), or can be isolated from a cell by a method comprising affinity chromatography using an anti-IKK-γ antibody.

Figure 1:
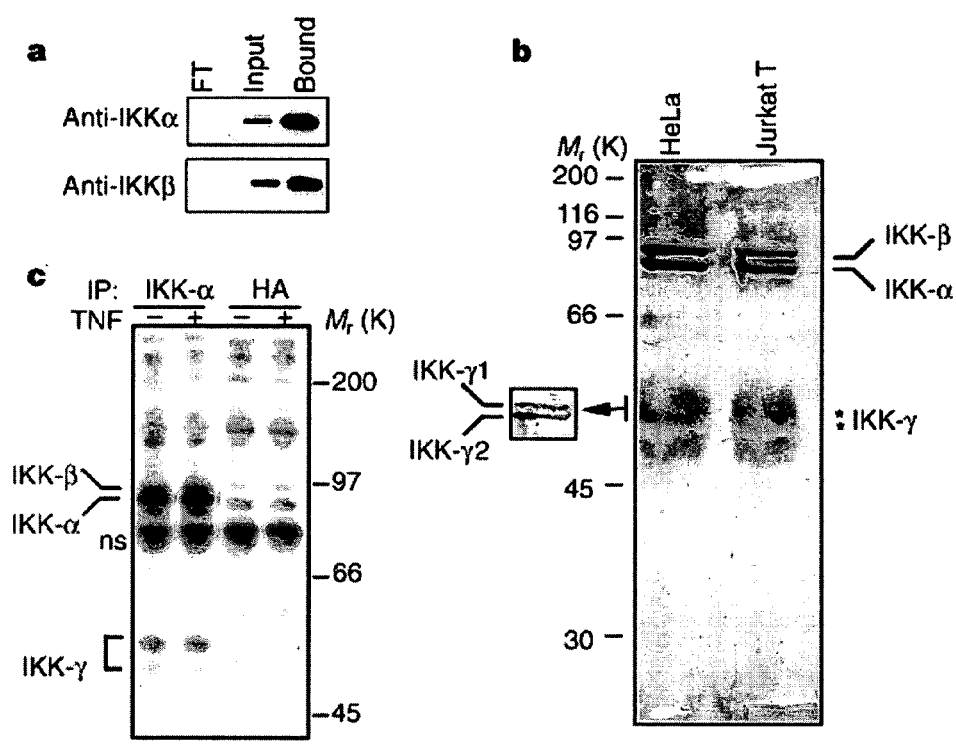
FIG. 1: Purification of the IKK complex and identification of the IKK subunits. a. Partially purified HeLa cell extracts were passed through an anti-IKK-α immunoaffinity column. The input, flowthrough (FT) and bound fractions were separated by SDS-PAGE and examined for IKK-α and IKK-β content by immunoblotting. b. The purified IKK complex was separated by SDS-PAGE and stained with colloidal blue. The positions of the different subunits are indicated. The inset shows a portion of a gel run for a longer time in which better separation of IKK-γ1 and IKK-γ2 is seen. c. 293 cells were labeled with $^{35}S$ for 5 hrs using Pro-Mix (Amersham) followed by incubation without or with TNF. Lysates were immunoprecipitated (IP) with either anti-IKK-α or anti-HA antibody (used as a control). After extensive washing, the immunecomplexes were separated by SDS-PAGE and visualized by autoradiography.

As used herein, the term "IKK-γ" means a polypeptide having substantially the same amino acid sequence as the human IKK-γ subunit (SEQ ID NO: 2) shown in FIG. 2b. The human IKK-γ subunit (SEQ ID NO: 2) is a polypeptide of 419 amino acids containing coiled-coil and leucine zipper α-helical regions, indicating that IKK-γ can be engaged in homotypic and heterotypic interactions. As illustrated in FIG. 1, an IKK-γ subunit can be human IKK-γ1 or IKK-γ2, which are polypeptides of 52 and 50 kDa molecular weight, respectively.

An IKK-γ having substantially the same amino acid sequence as SEQ ID NO: 2 can be a naturally occurring IKK-γ subunit such as IKK-γ1 or IKK-γ2 or a related polypeptide having substantial amino acid sequence similarity to SEQ ID NO: 2. Such related polypeptides include isotype variants, differentially spliced or initiated forms, and species homologs of the human IKK-γ amino acid sequence shown in FIG. 2b. As used herein, the term IKK-γ subunit describes polypeptides generally having an amino acid sequence with greater than about 35% amino acid identity, preferably greater than about 45% amino acid identity, more preferably greater than about 55% amino acid identity, and also describes polypeptides having greater than about 65%, 75%, 85%, 90%, 95%, 97%, or 99% amino acid sequence identity with SEQ ID NO: 2, said amino acid identity determined with CLUSTALW using the BLOSUM 62 matrix with default parameters.

As used herein, the term "substantially the same amino acid sequence," when used in reference to an IKK-γ subunit, is intended to mean a sequence as shown in FIG. 2b, or a similar, non-identical sequence that is considered by those skilled in the art to be a functionally equivalent amino acid sequence. For example, an amino acid sequence that has substantially the same amino acid sequence as human IKK-γ (SEQ ID NO: 2) can have one or more modifications such as amino acid additions, deletions or substitutions relative to the amino acid sequence of SEQ ID NO: 2, provided that the modified polypeptide retains substantially at least one biological activity of IKK-γ such as the ability to interact with IKK-α/β in cells; IKK-β binding activity; IKK-α binding activity; IKK regulatory activity, for example, the ability to interact with a factor required for IKK activation by TNF; or dimerization or trimerization activity, described further below. Comparison for substantial similarity between amino acid sequences is usually performed with sequences between about 6 and 100 residues, preferably between about 10 and 100 residues and more preferably between about 25 and 35 residues.

Thus, it is understood that limited modifications can be made to an IKK-γ subunit, or to an active fragment thereof, as described further below, without destroying its biological function. A modification of an IKK-γ subunit that does not destroy biological activity, such as IKK-β binding activity, is encompassed within the meaning of the term IKK-γ subunit, as used herein. A modification can be, for example, an addition, deletion, or conservative or non-conservative substitution of one or more amino acid residues; substitution of a compound that mimics amino acid structure or function; or addition of chemical moieties such as amino or acetyl groups. The activity of a modified IKK-γ subunit can be assayed as disclosed herein (see Examples).

In one embodiment, the invention provides an isolated IKK-γ subunit having substantially the same amino acid sequence as SEQ ID NO: 2, provided that the subunit does not include the amino acid sequence available as accession number AF069542. Thus, the invention provides, for example, an isolated IKK-γ subunit having at least 35%, 45%, 55%, 65%, 75%, 85%, 90%, 95%, 97%, or 99% amino acid identity with SEQ ID NO: 2, provided that the subunit does not include the amino acid sequence available as accession number AF069542. The cDNA sequence of NEMO (NF-κB Essential Modulator) is reported as accession number AF069542 and also described in Yamaoka et al., supra, 1998.

Figure 7:
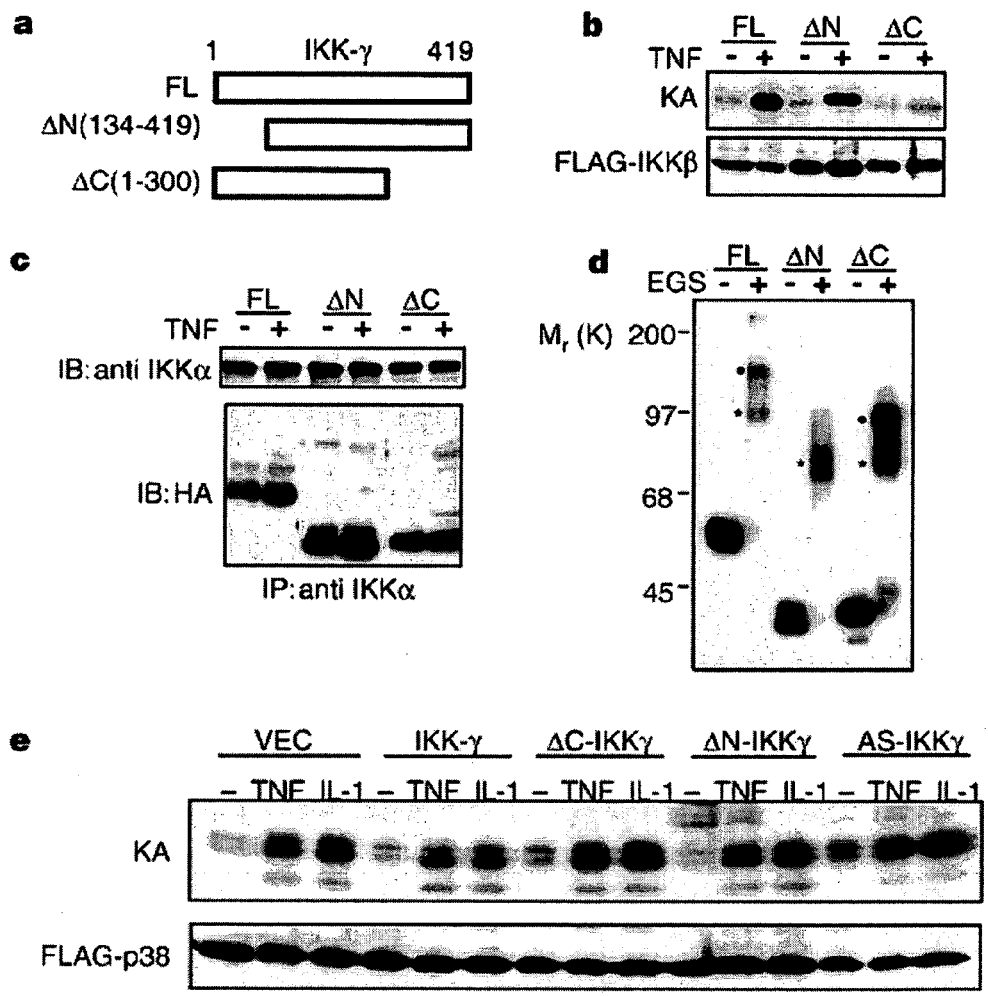
FIG. 7: A C-terminal IKK-γ deletion mutant is a dominant negative inhibitor of IKK activation. a. Schematic representation of full length (FL) IKK-γ and its deletion mutants. b. Flag-IKK-β was cotransfected with wild type and truncated IKK-γ expression vectors into HeLa cells. After 24 hrs cells were incubated or not with TNF and lysed. The lysates were immunoprecipitated with anti-Flag(M2) and IKK kinase activity (KA) and Flag-IKK-β expression were determined. c. 293 cells were transfected with the different HA-IKK-γ vectors and treated as described above. Lysates were immunoprecipitated with anti-IKK-α antibody and immunoblotted (IB) with anti-IKK-α and anti-HA antibodies. d. Recombinant full length IKK-γ and its truncation mutants were expressed in *E. coli*, purified and incubated with or without the crosslinking agent ethylene glycolbis (succinimidylsuccinate) (EGS). The proteins were separated by SDS-PAGE and visualized by immunoblotting. The asterisk and dot mark the dimer and trimer bands, respectively. e. Flag-p38 vector was cotransfected with either "empty" vector (VEC) or the different IKK-γ sense and antisense expression vectors. After 24 hrs the cells were either left untreated or incubated with TNF or IL-1. Lysates were prepared, p38 activity and expression were determined by immunecomplex kinase assay (KA) and immunoblotting, respectively.

As further disclosed herein, N- and C-terminal deletion derivatives of IKK-γ (SEQ ID NO: 2) were generated and assayed for the ability to effect TNF-responsive and basal IKK kinase activity. Although coexpression of ΔN-IKK-γ (134–419) with FLAG-IKK-β had only a marginal effect on basal IKK activity and its response to TNF, expression of ΔC-IKK-γ (1–300) inhibited activation of IKK by TNF but not basal kinase activity (FIG. 7b). In addition, both ΔN-IKK-γ (134–419) and ΔC-IKK-γ (1–300) retained the ability to interact with IKKα/β in cells (FIG. 7c). The ability of the C-terminally truncated IKK-γ derivative to inhibit IKK activation by upstream stimuli, while having only a small effect on basal kinase activity, indicates that IKK-γ can function to connect the IKK complex to upstream activators. The TNF responsive activity of the IKK can be mediated by the C-terminal region of IKK-γ, while the ability to bind IKK-β can reside in the central region of the subunit.

Thus, the invention also provides IKK-γ active fragments that have substantially the same amino acid sequence as a portion of the IκB kinase subunit, IKK-γ. An IKK-γ active fragment of the invention can contain, for example, ten, twenty, fifty or more contiguous amino acids of the human IKK-γ sequence disclosed herein as SEQ ID NO: 2.

As used herein, the term "IKK-γ active fragment" means a peptide or polypeptide which has substantially the same amino acid sequence as a portion of an IKK-γ subunit, provided that the fragment retains at least one biological activity of the IKK-γ subunit. A portion of an IKK-γ subunit generally has an amino acid sequence of 15 to 400 contiguous residues and can have, for example, an amino acid sequence of at least 18, 20, 25, 30, 35, 40, 50, 100, 150, 200, 250, 300, 350 or 400 contiguous residues. An IKK-γ active fragment can have a length, for example, of 18 to 30 residues, 18 to 40 residues, 18 to 50 residues, 18 to 100 residues, 18 to 200 residues, 25 to 40 residues, 25 to 50 residues, 25 to 100 residues, 25 to 200 residues, 35 to 50 residues, 35 to 100 residues or 35 to 200 residues.

An IKK-γ active fragment has one or more biological activities of full-length IKK-γ such as the ability to interact with IKK-α/β in cells; IKK-β binding activity; IKK-α binding activity; IKK regulatory activity, for example, the ability to interact with a factor required for IKK activation by TNF; or dimerization or trimerization activity. As disclosed herein, an IKK-γ subunit can interact physically with IKK-α/β as demonstrated by co-precipitation of HA tagged IKK-γ with endogenous IKK-α as disclosed in Example II. The IKK-γ deletion derivatives ΔN-IKK-γ (134–419) and ΔC-IKK-γ (1–300), which contain residues 134 to 419 and residues 1 to 300 of SEQ ID NO: 2, respectively, retained the ability to interact with IKK-α/β in cells as disclosed in Example IV (see FIG. 7c) and are exemplary IKK-γ active fragments.

Full-length IKK-γ can form dimers and trimers as demonstrated by ethylene glycol bis (succinimidylsuccinate) (EGS) cross-linking and shown in FIG. 7d. Dimerization activity was retained by ΔN-IKK-γ (134–419) and ΔC-IKK-γ (1–300), although trimerization of ΔN-IKK-γ (134–419) appeared to diminish. A fragment that has substantially the same amino acid sequence as a portion of an IKK-γ subunit and retains IKK-γ dimerization or trimerization activity also is an IKK-γ active fragment of the invention.

A biological activity of IKK-γ also can be the ability to directly bind IKK-β. As disclosed in Example II, full-length human IKK-γ and the deletion derivatives ΔN-IKK-γ (134–419) and ΔC-IKK-γ (1–300) were shown to stably and directly bind IKK-β by co-immunoprecipitation of purified recombinant proteins. Thus, a fragment of IKK-γ that has substantially the same amino acid sequence as a portion of an IKK-γ subunit can have IKK-β binding activity and, thus, be an IKK-γ active fragment as defined herein.

A biological activity of IKK-γ also can be the ability to bind directly or indirectly to IKK-α. As disclosed herein, an IKK-γ subunit can interacti physically with IKK-α/β. Furthermore, IKK-γ can form a complex with IKK-α in cells even in the absence of IKK-β. Thus, an IKK-γ fragment that has IKK-α binding activity also is an active fragment of the invention.

Figure 5:
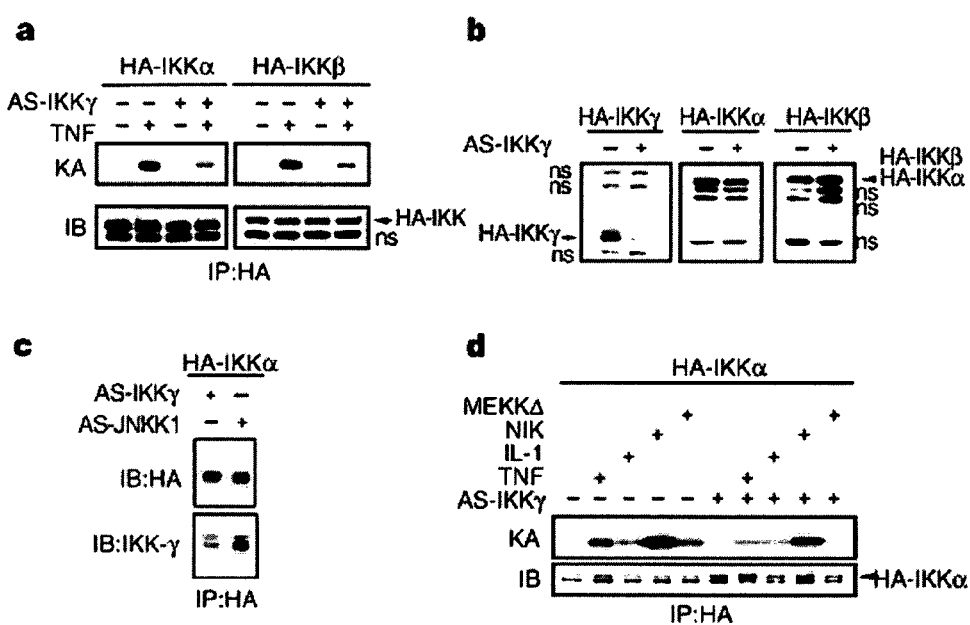
FIG. 5: IKK-γ is an essential component of the IκB kinase. a. HA-IKK-α and HA-IKKβ vectors were cotransfected into HeLa cells with either "empty" or antisense (AS)-IKK-γ vectors. After 24 hrs, cells were treated or not with TNF and lysed. Lysates were precipitated with anti-HA antibody and IKK activity was determined by immunocomplex kinase assays (KA). Expression of HA-IKK-α and HA-IKK-β was determined by immunoblotting (IB). Migration positions of IKK-α and IKK-β and a nonspecific (ns) band are indicated. b. HA-IKK-γ, HA-IKK-α or HA-IKK-β vectors were cotransfected into 293 cells with either "empty" or AS-IKK-γ vectors as indicated. After 24 hrs the cells were lysed, immunoprecipitated with anti-HA and immunoblotted with anti-HA antibody. "ns" designates nonspecific bands. c. HeLa cells were cotransfected with HA-IKK-α, and either AS-IKK-γ or AS-JNKK1 vectors. After 24 hrs, cell lysates were prepared, immunoprecipitated with anti-HA antibody and immunoblotted with anti-HA (top panel) or anti-NEMO (anti-IKKγ) antibody (bottom panel). d. HeLa cells were cotransfected with HA-IKK-α and either "empty" or AS-IKK-γ vectors, along with NIK or MEKK1 catalytic domain (MEKKΔ) expression vectors as indicated. After 24 hrs some cells were treated with TNF or IL-1, lysed and immunoprecipitated with anti-HA antibody. IKK activity was determined as above.

As further disclosed herein, the level of TNF-induced IκB kinase activity associated with either IKK subunit decreased upon co-transfection with an IKK-γ antisense vector (FIG. 5a). Furthermore, IKK-γ fragments can inhibit IKK activation by stimuli such as TNF while negligibly effecting basal kinase activity, indicating that one biological function of full-length IKK-γ is the ability to interact with an upstream activator such as an activator required for TNF-inducible IKK kinase activity. Thus, an IKK-γ active fragment also can be a fragment that has substantially the same amino acid sequence as a portion of an IKK-γ subunit and IKK kinase regulatory activity.

In one embodiment, an "IKK-γ active fragment" is a polypeptide portion having substantially the same amino acid sequence as a portion of an IKK-γ, provided that the fragment does not consist of the identical amino acid sequence encoded by an expressed sequence tag having accession number AA133061 and R56495, and provided that the fragment retains at least one biological activity of an IKK-γ subunit. Such an IKK-γ active fragment can have, for example, an amino acid sequence that is identical or substantially the same as a portion of the amino acid sequence of human IKK-γ (SEQ ID NO:2), provided that the segment does not consist of the identical amino acid sequence encoded by an expressed sequence tag having accession number AA133061 and R56495, and provided that the fragment retains at least one biological activity of an IKK-γ subunit.

IKK-γ active fragments can be identified by screening a large collection, or library, of peptides of interest for IKK-γ biological activity such as one of the IKK-γ biological activities described hereinabove. For example, a panel of peptides spanning the entire sequence of an IKK-γ subunit polypeptide such as the human IKK-γ shown as SEQ ID NO: 2 can be screened for the ability to interact with IKK-α/β in cells; dimerization or trimerization activity; IKK-β binding activity; IKK-α binding activity; IKK regulatory activity; or other IKK-γ biological activity as described below. Such a panel can be, for example, a panel of 15-mer peptides spanning the sequence of human IKK-γ (SEQ ID NO: 2), each overlapping by three or five residue shifts using the Mimotope cleavable pin technology (Cambridge Research Biochemicals, Wilmington, Del.), as described by Geysen et al., Science 235:1184 (1987)). The panel is subsequently screened for IKK-β binding activity or other IKK-γ biological activity as described hereinabove. A library of peptides to be screened also can be a population of peptides related in amino acid sequence to SEQ ID NO: 2 but having one or more amino acids that differ from SEQ ID NO: 2, for example, one or more conservative or non-conservative substitutions.

Additional peptides to be screened for IKK-γ biological activity to identify active fragments include, for example, tagged chemical libraries of peptides and peptidomimetic molecules. Peptide libraries encompass those generated by phage display technology, which is a technology that includes the expression of peptide molecules on the surface of phage as well as other methodologies by which a protein ligand is or can be associated with the nucleic acid which encodes it. Methods for production of phage display libraries, including vectors and methods of diversifying the population of peptides which are expressed, are well known in the art (see, for example, Smith and Scott, Methods Enzymol. 217:228–257 (1993); Scott and Smith, Science 249:386–390 (1990); and Huse, WO 91/07141 and WO 91/07149). These or other well known methods can be used to produce a phage display library which can be screened, for example, with one of the disclosed assays for an IKK-γ biological activity, for example, IKK-β binding activity. If desired, a population of peptides can be assayed for activity en masse. For example, to identify an active fragment of an IKK-γ subunit with IKK-β binding activity, a population of peptides can be assayed for the ability to specifically bind IKK-β; the active population can be subdivided and the assay repeated in order to isolate the IKK-γ active fragment from the population.

IKK-γ active fragments also can be identified by screening, for example, fragments of the polypeptide produced by chemical or proteolytic cleavage. Methods for chemical and proteolytic cleavage and for purification of the resultant protein fragments are well known in the art (see, for example, Deutscher, Methods in Enzymology, Vol. 182, "Guide to Protein Purification," San Diego: Academic Press, Inc. (1990)). For example, a chemical such as cyanogen bromide or a protease such as trypsin, chymotrypsin, V8 protease, endoproteinase Lys-C, endoproteinase Arg-C or endoproteinase Asp-N can be used to produce convenient fragments of an IKK-γ subunit that can be screened for biological activity using one of the assays disclosed herein.

As used herein, the term "fragment" means a peptide, polypeptide or compound containing naturally occurring amino acids, non-naturally occurring amino acids or chemically modified amino acids. An IKK-γ active fragment also can be a peptide mimetic, which has a non-amino acid chemical structure that mimics the structure of a peptide having an amino acid sequence, provided that the mimetic retains at least one biological activity of an IKK-γ subunit. Such a mimetic generally is characterized as exhibiting similar physical characteristics such as size, charge or hydrophobicity in the same spatial arrangement found in its peptide counterpart. A specific example of a peptide mimetic is a compound in which the amide bond between one or more of the amino acids is replaced, for example, by a carbon—carbon bond or other bond well known in the art (see, for example, Sawyer, *Peptide Based Drug Design*, ACS, Washington (1995)).

As used herein, the term "amino acid" refers to one of the twenty naturally occurring amino acids, including, unless stated otherwise, L-amino acids and D-amino acids. The term amino acid also refers to compounds such as chemically modified amino acids including amino acid analogs, naturally occurring amino acids that are not usually incorporated into proteins such as norleucine, and chemically synthesized compounds having properties known in the art to be characteristic of an amino acid, provided that the compound can be substituted within a peptide such that it retains at least one biological activity of IKK-γ. Examples of amino acids and amino acids analogs are listed in Gross and Meienhofer, *The Peptides: Analysis., Synthesis, Biology*, Academic Press, Inc., New York (1983). An amino acid also can be an amino acid mimetic, which is a structure that exhibits substantially the same spatial arrangement of functional groups as an amino acid but does not necessarily have both the α-amino and α-carboxyl groups characteristic of an amino acid.

An IKK-γ active fragment can be produced or synthesized using methods well known in the art. Such methods include recombinant DNA methods and chemical synthesis methods for production of a peptide. Recombinant methods for producing a peptide through expression of a nucleic acid sequence encoding the peptide in a suitable host cell are well known in the art and are described, for example, in Sambrook et al., *Molecular Cloning: A Laboratory Manual*, 2nd Ed, Vols 1 to 3, Cold Spring Harbor Laboratory Press, New York (1989). The sequence of a nucleic acid molecule encoding a human IKK-γ subunit is disclosed herein as SEQ ID NO: 1.

An IKK-γ active fragment also can be produced by chemical synthesis, for example, by the solid phase peptide synthesis method of Merrifield et al., *J. Am. Chem. Soc.* 85:2149 (1964). Standard solution methods well known in the art also can be used to synthesize an IKK-γ active fragment having IKK-β binding activity or other IKK-γ biological activity as disclosed herein (see, for example, Bodanszky, *Principles of Peptide Synthesis*, Springer-Verlag, Berlin (1984) and Bodanszky, *Peptide Chemistry*, Springer-Verlag, Berlin (1993)). A newly synthesized peptide can be purified, for example, by high performance liquid chromatography (HPLC), and can be characterized using, for example, mass spectrometry or amino acid sequence analysis.

Also provided herein are nucleic acid molecules encoding the IKK-γ subunit of the invention. These nucleic acid molecules are useful, for example, in producing recombinant polypeptides and as probes for diagnosing diseases involving aberrant expression of an IKK-γ subunit.

Thus, the invention provides isolated IKK-γ nucleic acid molecules, which contain a nucleotide sequence encoding substantially the same amino acid sequence as SEQ ID NO: 2, provided that the nucleic acid molecules do not consist of the identical nucleic sequence of an expressed sequence tag having accession number AA133061 or R56495. Such isolated IKK-γ nucleic acid molecules of the invention can have, for example, a nucleotide sequence encoding an amino acid sequence having at least 55% amino acid identity with SEQ ID NO: 2. An isolated IKK-γ nucleic acid molecule of the invention can have a nucleotide sequence encoding SEQ ID NO: 2, for example, nucleotides 149 to 1408 of SEQ ID NO: 1 or the entire sequence of SEQ ID NO: 1. An exemplary IKK-γ nucleic acid molecule of the invention is the human IKK-γ nucleic acid molecule provided herein as SEQ ID NO: 1 in FIG. 2a.

In one embodiment, the invention provides an isolated IKK-γ nucleic acid molecule, which contains a nucleotide sequence encoding substantially the same amino acid sequence as SEQ ID NO: 2, provided that the nucleic acid molecule does not consist of the identical nucleic sequence of a sequence having accession number AA133061, R56495 or AF069542.

The term "isolated," as used herein in reference to a nucleic acid molecule of the invention, means a nucleic acid molecule that is in a form that is relatively free from contaminating lipids, polypeptides, unrelated nucleic acids and other cellular material normally associated with a nucleic acid molecule in a cell.

Isolated nucleic acid molecules of the invention also include, for example, nucleic acid molecules encoding species homologs of human IKK-γ such as bovine, monkey, rat, mouse and other mammalian homologs, or other homologs such as chicken or xenopus homologs. Isolated IKK-γ nucleic acid molecules of the invention also include nucleic acid molecules that encode exactly the polypeptide of SEQ ID NO: 2 and are related but different from SEQ ID NO:1 due to the degeneracy of the genetic code. An IKK-γ nucleic acid molecule of the invention also can encode an IKK-γ subunit having a sequence that is different from SEQ ID NO:2, for example, containing one or more conservative or non-conservative amino acid substitutions relative to the amino acid sequence shown as SEQ ID NO: 2, provided that the encoded IKK-γ subunit retains at least one biological activity of IKK-γ. The invention also provides nucleic acid molecules encoding IKK-γ active fragments, described hereinabove.

An IKK-γ nucleic acid molecule of the invention can have a nucleotide sequence of, for example, 15 to 1200 or more nucleotides. In particular, a nucleic acid molecule of the invention can have a sequence of at least 15, 18, 20, 25, 30, 35, 50, 100, 200, 500 or more nucleotides.

Further provided by the invention are IKK-γ polynucleotides and antisense polynucleotides, which can be useful as probes and primers and to reduce IKK-γ expression in a cell. A polynucleotide of the invention contains at least nine contiguous nucleotides of the human IKK-γ sequence shown as SEQ ID NO: 1. An antisense polynucleotide of the invention contains a nucleotide sequence complementary to at least nine contiguous nucleotides of SEQ ID NO: 1. As defined herein, a polynucleotide of the invention is not the nucleotide sequence of accession number AA133061 or R56495.

As used herein, the term "polynucleotide" is used in its broadest sense to mean two or more nucleotides or nucleotide analogs linked by a covalent bond and refers to sense and antisense nucleotide sequences and encompasses both single-stranded and double-stranded molecules. The term "oligonucleotide" also is used herein to mean two or more nucleotides or nucleotide analogs linked by a covalent bond, although those in the art will recognize that oligonucleotides generally are less than about fifty nucleotides in length and, therefore, are a subset within the broader meaning of the term "polynucleotide."

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can comprise nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220–5234 (1994); Jellinek et al., *Biochemistry* 34:11363–11372 (1995); Pagratis et al., *Nature Biotechnol.* 15:68–73 (1997)). The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977–986 (1994); Ecker and Crooke, *BioTechnology* 13:351360 (1995)).

Where it is desired to synthesize a polynucleotide of the invention, the artisan will know that the selection of particular nucleotides or nucleotide analogs and the covalent bond used to link the nucleotides will depend, in part, on the purpose for which the polynucleotide is prepared. For example, where a polynucleotide will be exposed to an environment containing substantial nuclease activity, the artisan will select nucleotide analogs or covalent bonds that are relatively resistant to the nucleases. A polynucleotide containing naturally occurring nucleotides and phosphodiester bonds can be chemically synthesized or can be produced using recombinant DNA methods using an appropriate polynucleotide as a template. In comparison, a polynucleotide containing nucleotide analogs or covalent bonds other than phosphodiester bonds generally will be chemically synthesized, although an enzyme such as T7 polymerase can incorporate certain types of nucleotide analogs and, therefore, can be used to produce such a polynucleotide recombinantly from an appropriate template (Jellinek et al., supra, 1995).

The polynucleotides of the invention can specifically hybridize to a nucleic acid molecule encoding IKK-γ or can hybridize to a related molecule. Such hybridizing polynucleotides are useful, for example, as probes, which can hybridize to a nucleic acid molecule encoding an IKK-γ subunit and allow the identification of the nucleic acid molecule in a sample. A polynucleotide of the invention is characterized, in part, in that it contains at least nine contiguous nucleotides of the sequence shown as SEQ ID NO: 1, such sequences being particularly useful as primers for the polymerase chain reaction (PCR). A polynucleotide of the invention also can have, for example, at least 10, 11, 12, 13, 14, 15, 16, 17, 18, 19, 20, 25, 30 or 40 contiguous nucleotides of SEQ ID NO: 1, such polynucleotides being useful as hybridization probes and primers for PCR. The polynucleotides of the invention are particularly useful in methods of diagnosing a pathology, for example, a human disease, characterized by aberrant IKK-γ expression. For convenience, such polynucleotides can be packaged in a kit, which can be made commercially available and can provide a standardized diagnostic assay.

The invention also provides antisense polynucleotides, which are complementary to a portion of a nucleic acid molecule encoding an IKK-γ subunit and can bind to and inhibit expression of the IKK-γ in a cell. As disclosed herein, expression of an antisense molecule complementary to the nucleotide sequence shown in SEQ ID NO: 1 inhibited expression of HA-IKK-γ but had no effect on expression of either HA-IKK-α or HA-IKK-β (Example III; FIG. 5B). Furthermore, the level of TNF-induced IκB kinase activity associated with either kinase subunit decreased upon co-transfection with an antisense molecule complementary to SEQ ID NO: 1. Thus, an antisense molecule of the invention can be useful for decreasing inducible IKK activity in a cell, thereby reducing or inhibiting the level of NF-κB mediated gene expression and ameliorating the severity of a disease involving NF-κB as described further below.

An antisense nucleic acid molecule of the invention can contain a sequence complementary to the entire coding sequence of an IKK-γ subunit such as a sequence complementary to SEQ ID NO: 1, provided the antisense sequence is not complementary in its entirety to the sequence of GenBank Accession number AA133061 or R56495.

Antisense methods involve introducing the nucleic acid molecule, which is complementary to and can hybridize to the target nucleic acid molecule, into a cell. An antisense nucleic acid molecule can be a chemically synthesized polynucleotide, which can be introduced into the target cells by methods of transfection, or can be expressed from a plasmid or viral vector, which can be introduced into the cell and stably or transiently expressed using well known methods (see, for example, Sambrook et al., *Molecular Cloning: A laboratory manual* (Cold Spring Harbor Laboratory Press 1989); Ausubel et al., *Current Protocols in Molecular Biology* (Green Publ., NY 1989)). One in the art understands that the ability of an antisense polynucleotide sequence to specifically hybridize to a target nucleic acid sequence depends, for example, on the degree of complementarity shared between the sequences, the GC content of the hybridizing molecules, and the length of the antisense polynucleotide, which can be at least ten nucleotides in length, generally at least thirty nucleotides in length or at least fifty nucleotides in length, and can be up to the full length of a nucleotide sequence of SEQ ID NO: 1 (see Sambrook et al., supra, 1989).

The present invention also provides a method of identifying an effective agent that modulates the specific association of an IKK-γ subunit and a second protein. Such agents can represent novel therapeutic agents with immunosuppressant, anti-inflammatory or anti-cancer activity. The method includes the steps of contacting the IKK-γ subunit and the second protein with an agent under conditions suitable for the specific association of the IKK-γ subunit and the second protein, and detecting an altered association of the IKK-γ subunit and the second protein in the presence of the agent, where the altered association identifies the agent as an effective agent that modulates the specific association of the IKK-γ subunit and the second protein. In a method of the invention, the contacting can be, for example, in vitro with an isolated IKK-γ subunit. Alternatively, the IKK-γ subunit can be contacted, for example, in a cell such as a mammalian cell or yeast cell in culture. In a method of the invention, an altered association can be detected by a variety of methods, for example, by measuring transcriptional activity of a reporter gene. In one embodiment, the second protein is IKK-β and an effective agent is identified that modulates the specific association of an IKK-γ subunit and an IKK-β subunit. In another embodiment, the second protein is IKK-α and an effective agent is identified that modulates the specific association of an IKK-γ subunit and an IKK-α subunit.

The ability of the human IKK-γ subunit to associate with IKK-α/β was demonstrated by co-precipitation of IKK-β with transiently expressed HA-IKK-γ. As further disclosed herein, purified recombinant IKK-γ binds to purified IKK-β, indicating that IKK-γ directly binds the β subunit of IKK. In addition, IKK-γ associates with IKK-α in a cell in the absence of IKK-β. The ability of an IKK-γ subunit to associate with other proteins also is indicated, for example, by the presence in the IKK-γ subunit of two different protein binding domains, a helix-loop-helix domain and a leucine zipper domain (see FIG. 2c).

A screening assay of the invention provides a means to identify an effective agent that modulates the specific association of an IKK-γ subunit and a second protein. As used herein, the term "modulate" or "alter" when used in reference to the specific association of an IKK-γ subunit and a second protein, means that the affinity of the association is increased or decreased with respect to a control level of association, which is the level of association in the absence of an agent. Agents that can alter the specific association of an IKK-γ subunit with a second protein can be useful for modulating the level of phosphorylation of IκB in a cell, which, in turn, modulates the activity of NF-κB in the cell and the expression of one or more genes regulated by NF-κB.

A screening assay of the invention is particularly useful to identify, from among a diverse population of agents, those effective agents that modulate the specific association of an IKK-γ subunit and a second protein. Methods for producing libraries containing diverse populations of molecules, including chemical or biological molecules such as simple or complex organic molecules, peptides, proteins, peptidomimetics, glycoproteins, lipoproteins, polynucleotides, antibodies and the like, are well known in the art (Huse, U.S. Pat. No. 5,264,563, issued Nov. 23, 1993; Blondelle et al., *Trends Anal. Chem.* 14:83–92 (1995); York et al., *Science* 274:1520–1522 (1996); Gold et al., *Proc. Natl. Acad. Sci. USA* 94:59–64 (1997); Gold, U.S. Pat. No. 5,270,163, issued Dec. 14, 1993). Such libraries also can be obtained from commercial sources.

A particularly useful effective agent can be an agent that mimics the IKK-γ recognition site present in the final 70 amino acids of IKK-γ. Such a structural analog of this IKK-γ region, or an active subpart thereof, can prevent an IKK complex from being activated by an upstream component that results in inducible kinase activity such as TNF-inducible activity. A particularly useful effective agent also can be agent such as an antibody or other binding agent that binds to the carboxy-terminal 70 amino acids of IKK-γ or otherwise prevents this region from being activated by an upstream component that results in inducible IKK kinase activity.

Since libraries of diverse molecules can contain as many as $10^{14}$ to $10^{15}$ different molecules, a screening assay of the invention provides a simple means for identifying those effective agents in the library that can modulate the specific association of an IKK-γ subunit and a second protein. In particular, a screening assay of the invention can be automated, which allows for high through-put screening of randomly designed libraries of agents to identify those particular agents that can modulate the ability of an IKK-γ subunit and a second protein to associate specifically.

A drug screening assay of the invention utilizes an IKK-γ subunit, which, when used in isolated form, can be prepared recombinantly, for example, by expressing a nucleic acid molecule encoding the amino acid sequence shown in SEQ ID NO: 2; or can be purified as disclosed herein using immunoaffinity chromatography on immobilized anti-IKK-α; or can utilize an IKK-γ subunit fusion protein such as an hemagglutinin (HA), glutathione-S-transferase (GST) or histidine$_6$ (HIS6) fusion protein, wherein the HA, GST or HIS6 is linked to the IKK-γ subunit and comprises a tag (see Example II). Such a IKK-γ subunit fusion protein is characterized, in part, by having an affinity for a solid substrate as well as having the ability to specifically associate with a second protein such as IKK-β. For example, where an HA-IKK-γ fusion protein is used in such a screening assay, the solid substrate can contain covalently attached anti-HA antibody, which is bound by the HA tag component of the fusion protein.

As used herein, the term "IKK-β" means a polypeptide that phosphorylates IκBα on serine-32 and serine-36 and has an apparent molecular mass of about 87 kDa. An IKK-β can have, for example, substantially the IKK-β amino acid sequence shown in Zandi et al., supra, 1997.

The term "IKK-α," as used herein, means a polypeptide that phosphorylates IκBα on serine-32 and serine-36 and has an apparent molecular mass of about 85 kDa. An IKK-α can have, for example, substantially the IKK-α amino acid sequence shown in Zandi et al., supra, 1997.

A variety of in vivo and in vitro screening assays for detecting an altered association are well known in the art. A drug screening assay to identify an effective agent that modulates the specific association of an IKK-γ subunit and a second protein can be performed by allowing, for example, the IKK-γ subunit, which can be a fusion protein, to bind to a solid support, then adding the second protein, for example IKK-β, and an agent to be tested, under conditions suitable for the association of the IKK-β with IKK-γ in the absence of a drug (see Example II). As appropriate, the IKK-γ subunit can be activated, for example by TNF, or inactivated as disclosed herein and, typically, the component not bound to a solid support is detectably labeled so as to facilitate identification of the association. Control reactions, which contain or lack either the IKK-γ subunit, second protein, or the agent also are performed. Following incubation of the reaction mixture, the amount of second protein specifically bound to the IKK-γ subunit in the presence of an agent can be determined and compared to the amount of binding in the absence of the agent so that effective agents that modulate the specific association can be identified.

In an in vitro screening assay of the invention, a component conveniently can be detectably labeled with a radionuclide, fluorescent label, enzyme, peptide epitope or other such moiety that facilitates a determination of the amount of association in a reaction. By comparing the amount of specific binding of an IKK-γ subunit to a second protein in the presence of an agent as compared to a control level of binding, an effective agent that increases or decreases specific binding of the IKK-γ subunit to a second protein can be identified. Thus, the disclosed drug screening assays provide a rapid and simple method for selecting effective agents that desirably modulate the specific association of an IKK-γ subunit and a second protein such as an IKK-β subunit. Such agents can be useful, for example, for decreasing the activity of NF-κB in a cell and, therefore, can be useful as medicaments for the treatment of a pathology due, at least in part, to aberrant NF-κB activity.

A two-hybrid system such as the yeast two hybrid system also can be used to screen a panel of agents to detect an altered association of an IKK-γ subunit with a second protein. Using a two hybrid system, an effective agent is identified by an altered level of transcription of a reporter gene (see Fields and Song, *Nature* 340:245–246 (1989)). For example, the level of transcription of a reporter gene due to the bridging of a DNA-binding domain/IKK-γ subunit hybrid and a transactivation domain/second protein hybrid can be determined in the absence and presence of an agent. An effective agent, which alters the specific association of an IKK-γ subunit and a second protein, can be identified by an altered level of reporter gene transcription as compared to a control level of transcription in the absence of the agent.

In some cases, an agent may not be able to cross the yeast cell wall and, therefore, cannot enter a yeast cell to alter the association of an IKK-γ subunit and a second protein. The use of yeast spheroplasts, which are yeast cells that lack a cell wall, can circumvent this problem (Smith and Corcoran, In Current Protocols in Molecular Biology (ed. Ausubel et al.; Greene Publ., NY 1989)). In addition, an agent, upon entering a cell, may require "activation" by a cellular mechanism that may not be present in yeast. Activation of an agent can include, for example, metabolic processing of the agent or a modification such as phosphorylation of the agent, which can be necessary to convert the agent into an effective agent. A yeast two hybrid system can be adapted for use in mammalian cells using well known methods as described, for example, in Fearon et al., Proc. Natl. Acad. Sci., USA 89:7958–7962 (1992); Sambrook et al., supra, 1989; and Ausubel et al., supra, 1989.

One skilled in the art understands that an effective agent can function directly or indirectly and by a variety of mechanisms to alter the specific association of a a IKK-γ subunit and a second protein. An effective agent can function, for example, as a competitor of the binding interaction between an IKK-γ subunit and a second protein such as IKK-β or a protein required for TNF inducible IKK kinase activity. For example, a peptide or peptidomimetic that mimics the structure of the IKK-β binding region of an IKK-γ subunit can be an effective agent that decreases the association of an IKK-γ subunit and a second protein. A truncated IKK-γ subunit that retains the ability to specifically associate with IKK-β or a protein required for TNF inducible IKK kinase activity is an example of an effective agent that can decrease the specific association of an IKK-γ subunit with a second protein by acting as a competitor of the binding interaction. A fragment of IKK-β or a protein required for TNF inducible IKK kinase activity also can be useful as an effective agent, providing that the fragment can alter the association of an IKK-γ subunit with a second protein. Such fragments, which can be peptides as small as about five amino acids, can be identified, for example, by screening a peptide library (see, for example, Ladner et al., U.S. Pat. No. 5,223,409) using one of the assays described herein.

An effective agent also can bind to an IKK-γ at a site distant from the site of interaction, thereby altering the three-dimensional conformation of the polypeptide such that the association of IKK-γ and a second protein is increased or decreased. An effective agent also can produce an altered association by promoting a modification such as phosphorylation of an IKK-γ subunit. In addition, an effective agent can sequester or alter the subcellular localization of an IKK-γ subunit, thereby modulating the effective concentration of the subunit and the extent to which it can associate with a second protein.

The present invention also provides a method of modulating NF-κB activity in a cell by contacting the cell with an effective agent that modulates the specific association of an IKK-γ subunit and a second protein. In a method of the invention, the second protein can be, for example, IKK-β. Further provided are methods of modulating NF-κB activity in a cell by introducing into the cell an IKK-γ antisense polynucleotide. The IKK-γ antisense polynucleotide can be expressed in the cell, for example, in a vector.

Inappropriate regulation of Rel/NF-κB transcription factors is associated with various human diseases. For example, many viruses, including human immunodeficiency virus-1 (HIV-1), herpes simplex virus-1 (HSV-1) and cytomegalovirus (CMV) contain genes regulated by a κB regulatory element and these viruses, upon infecting a cell, utilize cellular Rel/NF-κB transcription factors to mediate viral gene expression (Siebenlist et al., supra, 1994). Tat-mediated transcription from the HIV-1 enhancer, for example, is decreased if the NF-κB and SP1 binding sites are deleted from the enhancer/promotor region, indicating that Tat interacts with NF-κB, SP1 or other transcription factors bound at this site to stimulate transcription (Roulston et al., *Microbiol. Rev.* 59:481–505 (1995)). In addition, chronic HIV-1 infection, and progression to AIDS, is associated with the development of constitutive NF-κB DNA binding activity in myeloid cells (Roulston et al., supra, 1995). Thus, a positive autoregulatory loop is formed, whereby HIV-1 infection results in constitutively active NF-κB, which induces expression of HIV-1 genes (Baeuerle and Baltimore, supra, 1996). Constitutive NF-κB activation also may protect cells against apoptosis, preventing clearance of virus-infected cells by the immune system (Liu et al., *Cell* 87:565–576 (1996)).

An effective agent that modulates the specific association of an IKK-γ subunit and a second protein such that IκB phosphorylation is decreased can be useful for reducing the severity of a viral infection such as HIV-1 infection in an individual by providing increased levels of unphosphorylated IκB in virus-infected cells. The unphosphorylated IκB then can bind to NF-κB in the cell, thereby preventing nuclear translocation of the NF-κB and viral gene expression. In this way, the rate of expansion of the virus population can be limited, thereby providing a therapeutic advantage to an individual infected with HIV.

In addition, decreased levels of NF-κB activity can allow virus-infected cell to undergo apoptosis, resulting in a decrease in the viral load in the individual. As such, it can be particularly useful to treat virus-infected cells ex vivo with an agent identified using a method of the invention. For example, peripheral blood mononuclear cells (PBMCs) can be collected from an HIV-1 infected individual and treated in culture with an effective agent that decreases the specific association of an IKK-γ subunit and a second protein. Such a treatment can be useful to purge the PBMCs of the virus-infected cells by allowing apoptosis to proceed. The purged population of PBMCs then can be expanded, if desired, and readministered to the individual.

Rel/NF-κB proteins also are involved in a number of different types of cancer. For example, the adhesion of cancer cells to endothelial cells is increased due to treatment of the cancer cells with IL-1, indicating that NF-κB induces expression of cell adhesion molecules, which mediate adherence of tumor cells to endothelial cells; agents such as aspirin, which decrease NF-κB activity, block adhesion by inhibiting expression of the cell adhesion molecules (Tozawa et al., *Cancer Res.* 55:4162–4167 (1995)). These results indicate that an agent that decreases the specific association of an IKK-γ subunit and a second protein can be useful for reducing the likelihood of metastasis of a tumor in an individual.

As discussed above for virus-infected cells, constitutive NF-κB activation also can protect tumor cells against programmed cell death as well as apoptosis induced by chemotherapeutic agents (Liu et al., supra, 1996; Baeuerle and Baltimore, supra, 1996). Thus, an agent that decreases the specific association of an IKK-γ subunit and a second protein can be useful in combination with an apoptosis inducing anti-cancer therapeutic, such as a chemotherapeutic agent, for allowing programmed cell death to occur in a tumor cell by increasing the level of unphosphorylated IκB, which can bind NF-κB and decrease the level of active NF-κB in the tumor cell. One skilled in the art understands that such effective agents can be particularly useful in treating tumors having elevated NF-κB activity.

NF-κB also plays a role in a variety of inflammatory diseases, for example, asthma, rheumatoid arthritis, inflammatory bowel diseases and psoriasis. In regard to asthma, for example, induction of the NF-κB target gene iNOS has been demonstrated in airway epithelium (Hamid et al., *Lancet* 342:1510–1513 (1993)); the exhaled air of asthmatic patients has a considerably higher NO content than that of normal individuals (Kharitonov et al., *Lancet* 343:133–135 (1994)). Furthermore, COX-2, also regulated by NF-κB, is expressed in higher levels at sites of inflammation, accounting for increased production of prostaglandins and thromboxanes (Barnes et al., supra, 1997). Asthma is associated with increased production of cytokines and chemokines that are activated by NF-κB, including IL-1β, TNF, IL-6, GM-CSF, and IL-8. Asthma attacks are triggered by viral infections and exposure to inhaled oxidants that activate NF-κB in the nasal epithelium and lungs of experimental animals (Haddad et al., *FEBS Lett.* 379:265–268 (1996)). Nuclear NF-κB was detected in inflammatory cells isolated from sputum and bronchial biopsies of asthmatic patients (Barnes et al., supra, 1997), and exposure of human lung tissue to proinflammatory cytokines resulted in prolonged NF-κB activation (Adcock et al., *Eur. Res. J.* 7:2117–2123 (1994)). In addition, glucocorticoids, which inhibit NF-κB activation, are an effective class of anti-inflammatory drugs for the treatment of asthma. Thus, NF-κB plays a role in inflammatory diseases such as asthma, and effective agents of the invention, which decrease IKK kinase activity and thereby decreased NF-κB activity, can be valuable therapeutics for the treatment of asthma.

As in asthma, NF-κB plays a role in the etiology of rheumatoid arthritis (RA). NF-κB is activated in synoviocytes of RA patients (Handel et al., *Arthritis Rheum.* 38:1762–1770 (1995); Marok et al., *Arthritis Rheum.* 39:583–591 (1996)). Transgenic mice that expression the potent NF-κB activator human T-cell leukemia virus (HTLV)-1 Tax protein develop RA-like symptoms (Nishioka et al., *Arthritis Rheum.* 39:1410–1418 (1996)). RA also involves increased synthesis of inflammatory mediators regulated by NF-κB and of the cell adhesion molecules ICAM-1, VCAM-1 and E-selectin, which are synthesized when NF-κB is activated (Arent et al., *Arthritis Rheum.* 38:151–160 (1995); Firestein et al., *J. Clin. Invest.* 96:1631–1638 (1995); McMurray, *Semin. Arthritis Rheum.* 25:215–233 (1996)). NF-κB inhibitors including glucocorticoids and salicylates are effective anti-arthritic drugs. Thus, NF-κB activation promotes RA, and effective agents of the invention identified as disclosed herein, can be useful as therapeutics for reducing the severity of inflammatory diseases such as rheumatoid arthritis.

Glucocorticoids are potent anti-inflammatory and immunosuppressive agents that are used clinically to treat various pathologic conditions, including autoimmune diseases such as rheumatoid arthritis, systemic lupus erythematosis and asthma. Glucocorticoids suppress the immune and inflammatory responses, at least in part, by increasing the rate of IκBα synthesis, resulting in increased cellular levels of IκBα, which bind to and inactivate NF-κB (Scheinman et al., *Science* 270:283–286 (1995); Auphan et al., *Science* 270:286–290 (1995)). Thus, glucocorticoids suppress NF-κB mediated expression of genes encoding, for example, cytokines, thereby suppressing the immune, inflammatory and acute phase responses. However, glucocorticoids and glucocorticoid-like steroids also are produced physiologically and are required for normal growth and development. Unfortunately, prolonged treatment of an individual with higher than physiological amounts of glucocorticoids produces clinically undesirable side effects. Thus, the invention provides alternative agents that can decrease the specific association of an IKK-γ subunit and a second protein and can provide a means for selectively decreasing NF-κB activity without producing some of the undesirable side effects associated with glucocorticoid treatment.

The methods of the invention involve contacting a cell with an effective agent that alters the specific association of an IKK-γ subunit with a second protein and can be performed by contacting cells in vitro or in vivo. Where the methods is performed with cells in vivo, the effective agent is administered to a subject. Based on the above, the skilled artisan will recognize that the methods of the invention are useful to treat, for example, patients with HIV-infection, cancer, asthma, rheumatoid arthritis or inflammatory bowel disease.

In the claimed methods of modulating NF-κB activity in a cell, an effective agent can be formulated, if desired, with a pharmaceutically acceptable carrier to produce a pharmaceutical composition, which can be administered to an individual such as a human or other mammal. A pharmaceutically acceptable carrier can be, for example, water, sodium phosphate buffer, phosphate buffered saline, normal saline or Ringer's solution or other physiologically buffered saline, or other solvent or vehicle such as a glycol, glycerol, an oil such as olive oil or an injectable organic ester.

A pharmaceutically acceptable carrier can contain, if desired, one or more physiologically acceptable compounds that act, for example, to stabilize or increase absorption of the effective agent. Such physiologically acceptable compounds include, for example, carbohydrates such as glucose, sucrose or dextrans; antioxidants such as ascorbic acid or glutathione; divalent metal ions such as calcium or magnesium; low molecular weight proteins; and other stabilizers or excipients. One skilled in the art would know that the choice of a pharmaceutically acceptable carrier, including a physiologically acceptable compound, depends, for example, on the route of administration of the composition.

A pharmaceutical composition containing an effective agent can be administered to an individual by various routes, including by intravenous, subcutaneous, intramuscular, intrathecal or intraperitoneal injection; orally, as an aerosol spray; or by intubation. If desired, the effective agent can be incorporated into a liposome, a non-liposome lipid complex, or other polymer matrix, which further can have incorporated therein, for example, a second drug useful for treating the individual. Liposomes, which consist of phospholipids or other lipids, are nontoxic, physiologically acceptable and metabolizable carriers that are relatively simple to make and administer (Gregoriadis, *Liposome Technology*, Vol. 1 (CRC Press, Boca Raton Fla., 1984)). The skilled artisan will select a particular route and method of administration based, for example, on the disease to be treated in a subject, and the specific effective agent that is administered.

In the methods of the invention for modulating NF-κB activity, an effective amount of the effective agent is administered. As used herein, the term "effective amount" refers to the amount of an effective agent that alters the specific association of an IKK-γ subunit with a second protein. In general, an effective amount of an effective agent produces minimal side effects, although the level of an acceptable deleterious effect is weighed against the benefit caused by the effective agent in treating, for example, a subject with HIV, cancer, asthma, rheumatoid arthritis or inflammatory bowel disease.

An effective agent can be administered to a subject such as a human systemically at a dose ranging from 1 to 100 mg/kg body weight, for example, at a dose of about 10 to 80 mg/kg, particularly about 10 to 50 mg/kg. An effective agent also can be incorporated into liposomes, if desired, in which case the total amount administered to a subject generally can be reduced. Furthermore, an effective agent can be administered orally to a subject at a dose ranging from about 1 to 100 mg/kg body weight, for example at a dose of about 10 to 200 mg/kg, in particular about 20 to 100 mg/kg. In addition, an effective agent can be administered topically to an environment, which can be a human subject, or can be placed in a solution, at a concentration of about 0.1 to 10 mg/ml, for example, at a concentration of about 0.5 to 5 mg/ml. The skilled artisan will recognize that the level of any side effects must be considered in prescribing a treatment regimen and must be monitored during the treatment period, and will adjust the amount of the effective agent that is administered accordingly.

The following examples are intended to illustrate but not limit the present invention.

EXAMPLE I

Isolation and Characterization of IKKγ

This example describes the isolation and characterization of a novel subunit of the IKK complex.

A. Purification of IKK-γ

To purify IKK to homogeneity, monoclonal antibodies specific for IKK-α were prepared. Using anti-IKK-α as an immunoaffinity reagent, the IKK complex was shown to contain nearly equal amounts of IKK-α and IKK-β in both HeLa and Jurkat cells (FIG. 1). Furthermore, passing partially purified IKK fractions through the anti-IKK-α column resulted in quantitative recovery of IKK-β (FIG. 1a), with which the antibody does not crossreact.

Large scale purification by combining the protocol described in DiDonato et al., supra, 1997, with immunoaffinity chromatography on immobilized anti-IKK-α revealed that, in addition to IKK-α and IKK-β, purified IKK contained two polypeptides of 50 and 52 kDa in size (FIG. 1b). Similar results were obtained by immunoprecipitation of $^{35}$S-labeled cell lysates (FIG. 1c). TNF treatment did not change the relative amounts of these polypeptides. Microsequencing of these polypeptides yielded the peptide sequence data shown in Table 1 and indicated that they are either differentially processed or initiated forms of the same protein, designated IKK-γ.

TABLE 1

Peptide sequence data for IKK$_γ$

| Sequence ID No. | Peptide Sequence | Source |
|---|---|---|
| 3 | IVMETVPVLK | HeLa GF |
| 4 | KELLQEQLEQLQREYSK | HeLa GF |
| 5 | ELLQEQLEQLQREYSK | HeLa GF |
| 6 | RHVEVSQAPLPPAPAYLSSP | HeLa GF |
| 7 | LAQLQVAYHQLFQEYDNHIK | HeLa GF |
| 8 | XQYQAPDMDTL | HeLa GF |
| 9 | XQPSGGPAADQDVLGEE | HeLa GF |
| 10 | QQLQQAEEALVAK | HeLa GF |
| 11 | EQALREVEHLK | HeLa GF |
| 12 | LVERLGLEK | HeLa GF |
| 13 | KELLQEQLEQLQREY | JURKAT IA LOWER |
| 14 | XXVTSLLGELQESQ | JURKAT IA LOWER |
| 15 | XXLQQAEEALVAK | HeLa IA LOWER |
| 16 | XQVTXLLXELQEXQQ | HeLa IA LOWER |
| 17 | XAQLQVAYHQLFQEYDNHIK | HeLa IA LOWER |

$^a$Peptides generated by endoproteinase Lys-C digest
$^b$Source of digested protein listing cell type, method of purification, and band location: GF -gel filtration; IA - immunoaffinity. LOWER and UPPER refer to the two bands labeled IKK-γ in FIG. 1.

Purification of IKK-γ was performed as follows. The IKK complex was purified from HeLa and Jurkat cells as described in DiDonato et al., supra, 1997, except for substituting affinity chromatography on an IκBα (1–54) column with affinity chromatography on immobilized monoclonal anti-IKK-α antibody (B78–743), generated against full length recombinant IKK-α and available from PharMingen (San Diego, Calif.). Purified antibody (0.5 mg) was coupled to 0.3 ml of CNBr-activated Sepharose 4B (Pharmacia). Active IKK fractions, after gel filtration on Superose 6, were pooled (1.6 ml) and applied batchwise to the immunoaffinity resin (0.1 ml). The mixture was rotated at 4° C. for 4 hrs and then centrifuged. The beads were washed with 20 ml of Buffer A prepared as in DiDonato et al, supra, 1997, containing 500 mM NaCl, 1% Triton X-100 followed by 5 ml of Buffer A containing 2 M urea. Bound protein was eluted with 0.5% SDS and separated by SDS-PAGE. Bands identified as IKK-γ were transferred to a PVDF membrane, stained with colloidal blue and digested with Lys-C. The IKK-γ1 band also was obtained in pure form after gel filtration and SDS-PAGE without requiring the immunoaffinity step. This material was transferred to a PVDF membrane and digested with Lys-C. A total of 15 peptide sequences derived from the 52 kDa (IKK-γ1) and 50 kDa (IKK-γ2) forms were obtained. All of these sequences were contained within the IKK-γ open reading frame (FIG. 2b). The peptide maps generated by Lys-C digestion of IKK-γ1 and IKK-γ2 were very similar.

These results demonstrate that, in addition to the IKK-α and IKK-β subunits, IKK contains two other major polypeptides, IKK-γ1 and IKK-γ2, that are derived from the same transcript.

B. Isolation of the IKK-γ cDNA

Screening of Genebank for identical or similar sequences revealed two overlapping expressed sequence tags (ESTs) with accession numbers AA133061 and R56495. A cDNA probe corresponding to these ESTs was used to isolate a cDNA clone containing the entire IKK-γ open reading frame from a HeLa library (FIGS. 2a and b). The complete IKK-γ nucleotide sequence is available under accession number AF074382. As shown in FIG. 2, the predicted IKK-γ polypeptide is a glutamine rich protein 419 amino acids in length with a predicted secondary structure containing two extended coil—coil motifs and a leucine zipper, each of which can function in protein—protein interactions (Berger et al., *Proc. Natl. Acad. Sci. USA* 92:8259–8263 (1995); Rost B., *Meth. Enzymol.* 266:525–539 (1996); Frishman and Argos, supra, 1996).

EXAMPLE II

IKK-γ Binds the IKK-β Component of IKK and Associates with IKK-α in the Absence of IKK-β

This example demonstrates that IKK-γ directly binds IKK-β and that IKK-γ can form a complex with IKK-α in IKK-β deficient cells.

A. IKK-γ Interacts Physically with IKK-α/β

Figure 3:
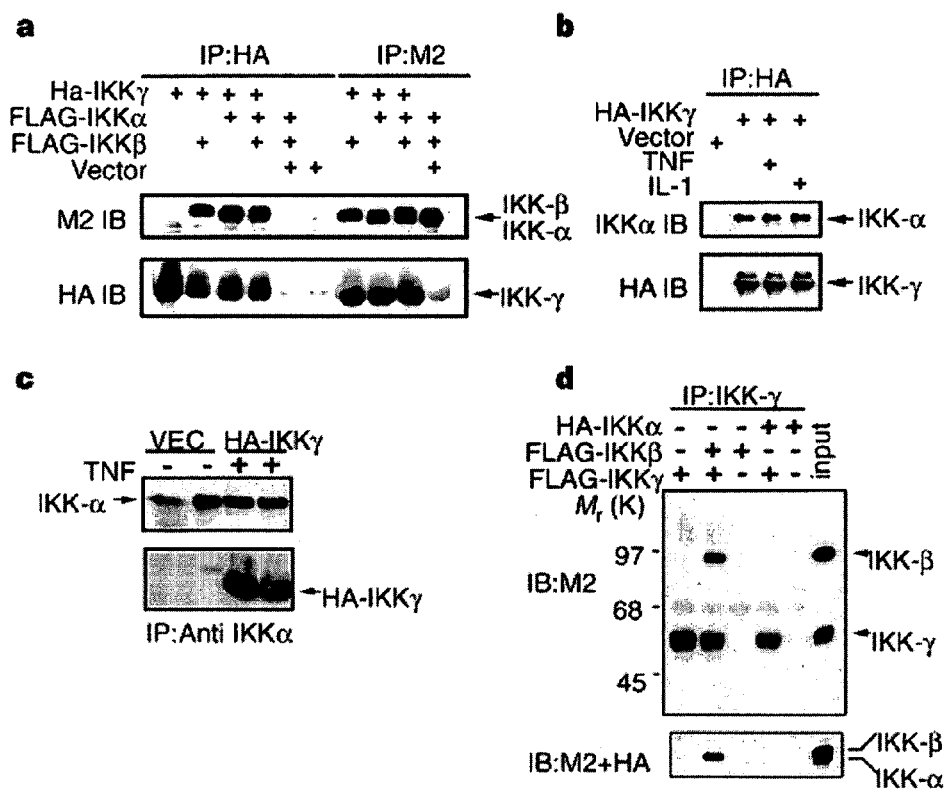
FIG. 3: IKK-γ physically interacts with IKK-α/β. a. HA-IKK-γ, Flag-IKK-α, Flag-IKK-β or empty expression vectors were transiently transfected into 293 cells as indicated. After 24 hrs the cells were lysed. Part of each lysate was precipitated with anti-HA antibody and another part with anti-Flag antibody (M2). The levels of Flag-IKK-α, Flag-IKK-β and HA-IKK-γ were determined by immunoblotting. b. HA-IKK-γ or "empty" vectors were transfected into HeLa cells. After 24 hrs the cells were left untreated or incubated with either TNF or IL-1, lysed, and immunoprecipitated with anti-HA antibody and immunoblotted with anti-IKK-α and anti-HA antibody. c. HA-IKK-γ or "empty" vectors (VEC) were transfected into 293 cells that were treated and processed as in b. d. HA-IKK-α and Flag-IKK-β were expressed in Sf9 cells using baculovirus vectors and purified as described in Zandi et al., *Science* 281:1360–1363 (1998). After incubation with or without purified recombinant Flag-IKK-γ, the proteins were immunoprecipitated with anti-IKK-γ (NEMO) antibody (Yamaoka et al., *Cell* 93:1231–1240 (1998)) and immunoblotted with anti-HA and anti-Flag(M2) antibody. "IP" designates immunoprecipitation; "IB" designates immunoblot.

To confirm that the cloned IKK-γ protein interacts with IKK-α/β subunits in cells, an expression vector for N-terminally hemagglutinin (HA)-tagged IKK-γ was cotransfected into HeLa cells with expression vectors for either Flag-IKK-α or Flag-IKK-β. Transfected cell lysates were immunoprecipitated with anti-HA followed by immunoblotting with anti-Flag. As shown in FIG. 3a, IKK-γ interacted efficiently with IKK-α and IKK-β. Similar results were obtained when the immuno-precipitating antibody was directed to the Flag epitope and the immunecomplexes were immunoblotted with anti-HA antibody recognizing the epitope on IKK-γ. Immunoprecipitation of transiently expressed HA-IKK-γ resulted in isolation of endogenous IKK-α (FIG. 3b). In addition, immunoprecipitation of endogenous IKK-α coprecipitated HA-IKK-γ (FIG. 3c). The interaction between IKK-γ and IKK-α was not modulated by cytokines (FIGS. 1c, 3b).

Cell culture, transfections, immunoprecipitation and immunoblotting were performed essentially as follows. The various expression vectors were constructed using standard recombinant DNA procedures. The β-actin promoter was used to drive expression of all sense IKK-γ constructs. Cell culture and transfections were as described in DiDonato et al., supra, 1997, except that Lipofectamine Plus (GIBCO) was used.

Immunoprecipitation and immunoblotting were performed as described in DiDonato et al., supra, 1997, and Zandi et al., supra, 1997. The monoclonal anti-IKK-α antibody, which does not cross-react with IKK-β, was used for immunoblotting and immunoprecipitation. TNF-α and IL-1 were used at 20 ng/ml and 10 ng/ml, respectively. Induction times were 10 min except where otherwise indicated in the Brief Description of Drawings.

B. Purified IKK-γ Directly Binds IKK-β.

IKK-α and IKK-β are known to form very stable heterodimers (Zandi et al, supra, 1998). Accordingly, the co-immunoprecipitation results indicate that IKK-γ binds directly to IKK-α, or directly to IKK-β, or directly to both proteins. The interaction of IKK-γ with IKK-α and IKK-β therefore was analyzed using purified recombinant proteins. As shown in FIG. 3d, direct and stable binding of IKK-γ to IKK-β was detected, although binding to IKK-α was not evident, potentially as a result of interference of epitope tags. These results indicate that IKK-γ directly binds IKK-β.

Recombinant proteins were expressed and purified as follows. Recombinant HA-IKK-α and Flag-IKK-β were expressed in Sf9 cells using recombinant baculovirus vectors and purified to homogeneity as described in Zandi et al., supra, 1998. Recombinant hexahistidine tagged IKK-γ proteins were expressed in *E. coli* and purified by nickel affinity chromatography.

C. IKK-γ Associates with IKK-α in the Absence of IKK-β

Lysates of IKK-$β^{+/+}$, IKK-$β^{+/-}$ and IKK-$β^{-/-}$ cells were prepared as described in Li et al., *J. Exp. Med.* 189: 1839–1845 (1999). The lysates were immunoprecipitated with either anti-IKK-α or anti-IKK-γ antibodies; dissolved in SDS loading buffer and separated by SDS-PAGE. After transfer to an Immobilon membrane, the proteins were analyzed by immunoblotting with anti-IKK-α antibody. A 3T3 cell lysate was used as a control.

The co-immunoprecipitation results showed that, in contrast to the results obtained with recombinant proteins, very efficient co-precipitation of IKK-α was achieved with anti-IKK-γ antibodies using lysates of IKK-$β^{-/-}$ cells as starting material, similar to the co-precipitation observed with IKK-$β^{+/+}$ cell lysates. These results indicate that IKK-γ can associate directly or indirectly with IKK-α and that IKK-β is not required for this association.

EXAMPLE III

IKK-γ is an Essential Component of the IκB Kinase

This example uses antisense methodology to demonstrate that IKK-γ is an essential component of the IκB kinase (IKK).

A. IKK-γ is an Essential Component of the IκB Kinase

Figure 4:
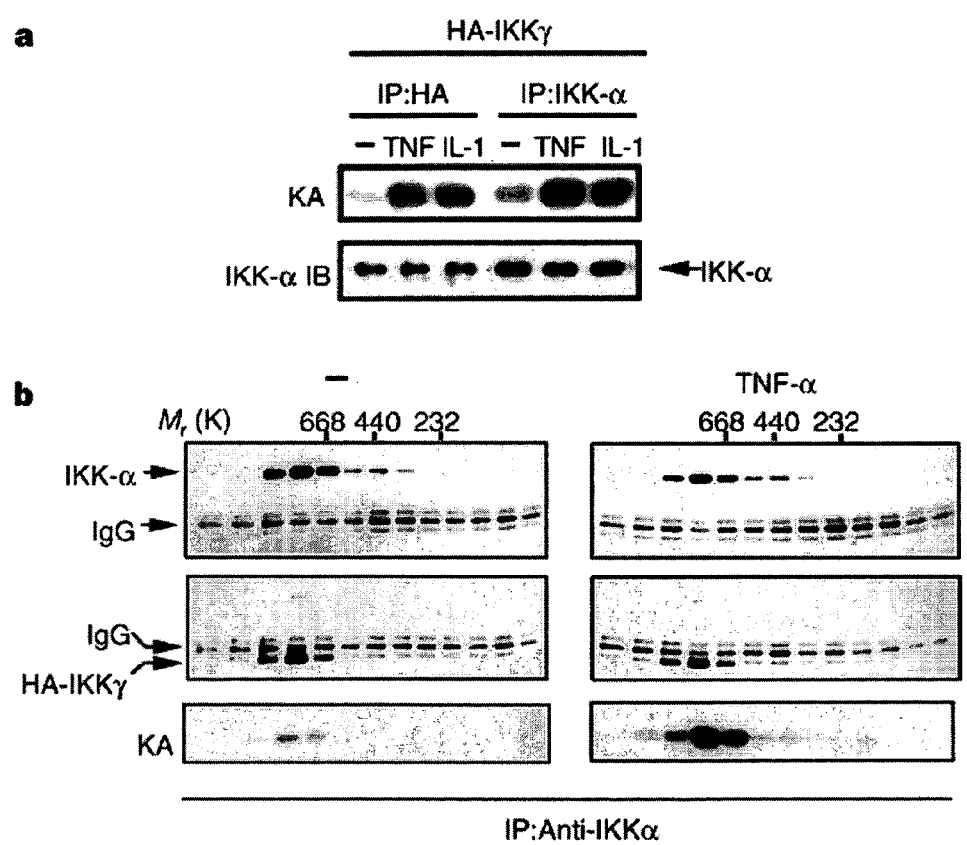
FIG. 4: IKK-γ is a component of the IκB kinase complex. a. HeLa cells were transiently transfected with HA-IKK-γ. After 24 hrs, cells were treated or not with TNF or IL-1. Part of each lysate was immunoprecipitated (IP) with anti-HA antibody and another part with anti-IKK-α; IκB kinase activity was determined as described in DiDonato et al., *Nature* 388:548–554 (1997). Levels of endogenous IKK-α were determined by immunoblotting (IB) with anti-IKK-α. b. Extracts of unstimulated or TNF treated 293 cells that were transfected with an HA-IKK-γ vector were fractionated on a Superose 6 column. Fractions were immunoprecipitated with anti-IKK-α antibody. Immunecomplex kinase assays (KA) and immunoblotting of IKK-α and HA-IKK-γ were conducted with IKK-α and HA antibodies.

Immunoprecipitation of HA-IKK-γ from transiently transfected cells resulted in isolation of an IκB kinase activity that was stimulated by either TNF or IL-1 (FIG. 4a) as was seen when anti-IKK-α was used to isolate the IKK complex. These results were identical to those obtained when anti-IKK-α was used to isolated the IKK complex. This similarity was due to efficient interaction between transiently expressed HA-IKK-γ and other IKK components. Gel filtration analysis indicated that HA-IKK-γ was incorporated into the large 900 kDa IKK complex, precisely coeluting with IKK-α (FIG. 4b).

The role of IKK-γ in IKK activation was analyzed using expression of IKK-γ antisense constructs made in pcDNA3.1/Myc-His (Invitrogen). Whereas cotransfection of an IKK-γ sense vector had no effect on IκB kinase activity associated with either IKK-α or IKK-β (see below), the level of TNF-induced IκB kinase activity associated with either IKK subunit decreased upon cotransfection with the IKK-γ antisense vector (FIG. 5a). Antisense IKK-γ reduced expression of HA-IKK-γ, but had no effect on expression of either HA-IKK-α or HA-IKK-β (FIG. 5b). Using anti-NEMO antibodies (Yamaoka et al., supra, 1998), transient expression of antisense IKK-γ RNA was shown to reduce expression of endogenous IKK-γ but not IKK-α (FIG. 5c) or IKK-β.

Antisense IKK-γ also reduced the extent of IKK activation by IL-1 or transiently transfected MEKKI or NIK vectors, although the inhibition of the response to overexpressed NIK was considerably weaker than that of the other responses (FIG. 5d). Cotransfection with antisense vectors for the kinases JNKK-1 or MKK-3 had no effect on IKK activity (DiDonato et al., supra, 1997), and antisense IKK-γ did not inhibit activation of p38$^{MAPK}$ by either TNF or IL-1 (FIG. 7e). Transient expression of antisense IKK-γ prevented TNF-induced nuclear entry of the RelA (p65) subunit of NF-κB.

B. Reduced IKK-γ Expression Interferes with IκBα Phosphorylation and Degradation and NF-κB Activation Stably transfected pools of 293 cells harboring the antisense IKK-γ expression vector were also established. Cells in these pools expressed lower levels of IKK-γ (FIG. 6b) and, in comparison to the parental cells, exhibited lower levels of TNF-induced IκBα phosphorylation and degradation (FIG. 6a) and NF-κB activation (FIG. 6c). This inhibitory effect was specific as IKK-α expression was not decreased (FIG. 6a) and the DNA binding activity of the constitutive transcription factor NF-1 was actually elevated in cells transfected with antisense IKK-γ (FIG. 6c). In addition, the antisense IKK-γ transfected cells exhibited normal activation of the kinases JNK and p38$^{MAPK}$ (FIG. 6d).

These results indicate that reduced IKK-γ expression interferes with IκBα phosphorylation and degradation and NF-κB activation.

EXAMPLE IV

Dominant Negative Inhibitors of IKK Activation

This example demonstrates that a C-terminal IKK-γ deletion mutant is a dominant negative inhibitor of IKK activation.

To study the function of IKK-γ, N- and C-terminal deletion mutants were constructed as described in Zandi et al., supra, 1997) and analyzed for possible dominant inhibitory activity (FIG. 7a). Coexpression of ΔN-IKK-γ (134–419) with FLAG-IKK-β had only a marginal effect on basal IKK activity and its response to TNF. However, expression of ΔC-IKK-γ (1–300) or ΔC-IKK-γ (1–349) inhibited activation of IKK by TNF but not basal kinase activity (FIG. 7b). ΔN-IKK-γ (134–419), ΔC-IKK-γ (1–300) and ΔC-IKK-γ (1–349) interacted with IKKα/β in cells (FIG. 7c), but only full length IKK-γ and ΔN-IKK-γ (134–419) were able to coprecipitate IKK activity stimulated by TNF, IL-1, MEKK-1 or NIK. Crosslinking experiments using recombinant proteins indicated that IKK-γ can form dimers and trimers and that the C-terminal truncation had no effect on this activity, although the N-terminal truncation may have reduced the efficiency of trimerization. Neither full-length IKK-γ nor its truncation mutants inhibited activation of p38$^{MAPK}$ by TNF or IL-1 (FIG. 7e).

These results indicate that the IKK-γ region responsible for interaction with an upstream factor required for TNF-inducible kinase activity resides in the 70 carboxy-terminal amino acids of IKK-γ.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

We claim:

1. An isolated human IKK-γ nucleic acid molecule comprising a nucleotide sequence encoding amino acid sequence SEQ ID NO:2.

2. The isolated human IKK-γ nucleic acid molecule of claim 1, comprising nucleotides 149 to 1408 of SEQ ID NO:1.

3. The isolated human IKK-γ nucleic acid molecule of claim 1, comprising SEQ ID NO:1.

4. An isolated antisense polynucleotide, comprising the nucleotide sequence complementary to nucleotides 149 to 1408 of SEQ ID NO:1.

5. An isolated human IKK-γ nucleic acid molecule encoding an IKK-γ deletion derivative, wherein said IKK-γ deletion derivative comprises amino acids 134 to 419 of SEQ ID NO:2.

6. An isolated human IKK-γ nucleic acid molecule encoding an IKK-γ deletion derivative, wherein said IKK-γ deletion derivative comprises amino acids 1 to 300 of SEQ ID NO:2.

* * * * *

SEQUENCE LISTING

<160> NUMBER OF SEQ ID NOS: 19

<210> SEQ ID NO 1
<211> LENGTH: 1994
<212> TYPE: DNA
<213> ORGANISM: Homo sapiens
<220> FEATURE:
<221> NAME/KEY: CDS
<222> LOCATION: (149)..(1408)

<400> SEQUENCE: 1

```
ggcacgagca tggcccttgt gatccaggtg gggaaactaa ggcccagaga agtgaggacc      60
ccgcagacta tcaatcccag tctcttcccc tcactccctg tgaagctctc cagcatcatc     120
gaggtcccat cagcccttgc cctgttgg atg aat agg cac ctc tgg aag agc       172
                                Met Asn Arg His Leu Trp Lys Ser
                                  1               5 caa ctg tgt gag atg gtg cag ccc agt ggt ggc ccg gca gca gat cag       220
Gln Leu Cys Glu Met Val Gln Pro Ser Gly Gly Pro Ala Ala Asp Gln
         10              15                  20 gac gta ctg ggc gaa gag tct cct ctg ggg aag cca gcc atg ctg cac       268
Asp Val Leu Gly Glu Glu Ser Pro Leu Gly Lys Pro Ala Met Leu His
 25                  30                  35                  40 ctg cct tca gaa cag ggc gct cct gag acc ctc cag cgc tgc ctg gag       316
Leu Pro Ser Glu Gln Gly Ala Pro Glu Thr Leu Gln Arg Cys Leu Glu
                 45                  50                  55 gag aat caa gag ctc cga gat gcc atc cgg cag agc aac cag att ctg       364
Glu Asn Gln Glu Leu Arg Asp Ala Ile Arg Gln Ser Asn Gln Ile Leu
             60                  65                  70 cgg gag cgc tgc gag gag ctt ctg cat ttc caa gcc agc cag agg gag       412
Arg Glu Arg Cys Glu Glu Leu Leu His Phe Gln Ala Ser Gln Arg Glu
```

```
                    75                  80                  85
gag aag gag ttc ctc atg tgc aag ttc cag gag gcc agg aaa ctg gtg        460
Glu Lys Glu Phe Leu Met Cys Lys Phe Gln Glu Ala Arg Lys Leu Val
     90                  95                 100 gag aga ctc ggc ctg gag aag ctc gat ctg aag agg cag aag gag cag        508
Glu Arg Leu Gly Leu Glu Lys Leu Asp Leu Lys Arg Gln Lys Glu Gln
105                 110                 115                 120 gct ctg cgg gag gtg gag cac ctg aag aga tgc cag cag cag atg gct        556
Ala Leu Arg Glu Val Glu His Leu Lys Arg Cys Gln Gln Gln Met Ala
                    125                 130                 135 gag gac aag gcc tct gtg aaa gcc cag gtg acg tcc ttg ctc ggg gag        604
Glu Asp Lys Ala Ser Val Lys Ala Gln Val Thr Ser Leu Leu Gly Glu
            140                 145                 150 ctg cag gag agc cag agt cgc ttg gag gct gcc act aag gaa tgc cag        652
Leu Gln Glu Ser Gln Ser Arg Leu Glu Ala Ala Thr Lys Glu Cys Gln
        155                 160                 165 gct ctg gag ggt cgg gcc cgg gcg gcc agc gag cag gcg cgg cag ctg        700
Ala Leu Glu Gly Arg Ala Arg Ala Ala Ser Glu Gln Ala Arg Gln Leu
    170                 175                 180 gag agt gag cgc gag gcg ctg cag cag cag cac agc gtg cag gtg gac        748
Glu Ser Glu Arg Glu Ala Leu Gln Gln Gln His Ser Val Gln Val Asp
185                 190                 195                 200 cag ctg cgc atg cag ggc cag agc gtg gag gcc gcg ctc cgc atg gag        796
Gln Leu Arg Met Gln Gly Gln Ser Val Glu Ala Ala Leu Arg Met Glu
                    205                 210                 215 cgc cag gcc gcc tcg gag gag aag agg aag ctg gcc cag ttg cag gtg        844
Arg Gln Ala Ala Ser Glu Glu Lys Arg Lys Leu Ala Gln Leu Gln Val
            220                 225                 230 gcc tat cac cag ctc ttc caa gaa tac gac aac cac atc aag agc agc        892
Ala Tyr His Gln Leu Phe Gln Glu Tyr Asp Asn His Ile Lys Ser Ser
        235                 240                 245 gtg gtg ggc agt gag cgg aag cga gga atg cag ctg gaa gat ctc aaa        940
Val Val Gly Ser Glu Arg Lys Arg Gly Met Gln Leu Glu Asp Leu Lys
    250                 255                 260 cag cag ctc cag cag gcc gag gag gcc ctg gtg gcc aaa cag gag gtg        988
Gln Gln Leu Gln Gln Ala Glu Glu Ala Leu Val Ala Lys Gln Glu Val
265                 270                 275                 280 atc gat aag ctg aag gag gag gcc gag cag cac aag att gtg atg gag       1036
Ile Asp Lys Leu Lys Glu Glu Ala Glu Gln His Lys Ile Val Met Glu
                    285                 290                 295 acc gtt ccg gtg ctg aag gcc cag gcg gat atc tac aag gcg gac ttc       1084
Thr Val Pro Val Leu Lys Ala Gln Ala Asp Ile Tyr Lys Ala Asp Phe
            300                 305                 310 cag gct gag agg cag gcc cgg gag aag ctg gcc gag aag aag gag ctc       1132
Gln Ala Glu Arg Gln Ala Arg Glu Lys Leu Ala Glu Lys Lys Glu Leu
        315                 320                 325 ctg cag gag cag ctg gag cag ctg cag agg gag tac agc aaa ctg aag       1180
Leu Gln Glu Gln Leu Glu Gln Leu Gln Arg Glu Tyr Ser Lys Leu Lys
    330                 335                 340 gcc agc tgt cag gag tcg gcc agg atc gag gac atg agg aag cgg cat       1228
Ala Ser Cys Gln Glu Ser Ala Arg Ile Glu Asp Met Arg Lys Arg His
345                 350                 355                 360 gtc gag gtc tcc cag gcc ccc ttg ccc ccc gcc cct gcc tac ctc tcc       1276
Val Glu Val Ser Gln Ala Pro Leu Pro Pro Ala Pro Ala Tyr Leu Ser
                    365                 370                 375 tct ccc ctg gcc ctg ccc agc cag agg agg agc ccc ccc gag gag cca       1324
Ser Pro Leu Ala Leu Pro Ser Gln Arg Arg Ser Pro Pro Glu Glu Pro
            380                 385                 390 cct gac ttc tgc tgt ccc aag tgc cag tat cag gcc cct gat atg gac       1372
```

```
Pro Asp Phe Cys Cys Pro Lys Cys Gln Tyr Gln Ala Pro Asp Met Asp
        395                 400                 405 acc ctg cag ata cat gtc atg gag tgc att gag tag ggccggccag          1418
Thr Leu Gln Ile His Val Met Glu Cys Ile Glu
        410                 415                 420 tgcaaggcca ctgcctgccc gaggacgtgc ccgggaccgt gcagtctgcg ctttcctctc   1478
ccgcctgcct agcccaggat gaagggctgg gtggccacaa ctgggatgcc acctggagcc   1538
ccacccagga gctggccgcg gcaccttacg cttcagctgt tgatccgctg gtcccctctt   1598
ttggggtaga tgcggccccg atcaggcctg actcgctgct cttttgttc ccttctgtct    1658 gctcgaacca cttgcctcgg gctaatccct ccctcttcct ccacccggca ctggggaagt   1718
caagaatggg gcctggggct ctcagggaga actgcttccc ctggcagagc tgggtggcag   1778
ctcttcctcc caccggacac cgacccgccc gccgctgtgc cctgggagtg ctgccctctt   1838
accatgcaca cggtgctct cctttggggc tgcatgctat tccatttgc agccagaccg     1898 atgtgtattt aaccagtcac tattgatgga catttgggtt gtttcccatc tttttgttac   1958
cataaataat ggcatagtaa aaaaaaaaaa aaaaaa                             1994
```

<210> SEQ ID NO 2
<211> LENGTH: 419
<212> TYPE: PRT
<213> ORGANISM: Homo sapiens

<400> SEQUENCE: 2

```
Met Asn Arg His Leu Trp Lys Ser Gln Leu Cys Glu Met Val Gln Pro
 1               5                  10                  15

Ser Gly Gly Pro Ala Ala Asp Gln Asp Val Leu Gly Glu Glu Ser Pro
                20                  25                  30

Leu Gly Lys Pro Ala Met Leu His Leu Pro Ser Glu Gln Gly Ala Pro
            35                  40                  45

Glu Thr Leu Gln Arg Cys Leu Glu Glu Asn Gln Glu Leu Arg Asp Ala
        50                  55                  60

Ile Arg Gln Ser Asn Gln Ile Leu Arg Glu Arg Cys Glu Glu Leu Leu
 65                 70                  75                  80

His Phe Gln Ala Ser Gln Arg Glu Glu Lys Glu Phe Leu Met Cys Lys
                85                  90                  95

Phe Gln Glu Ala Arg Lys Leu Val Glu Arg Leu Gly Leu Glu Lys Leu
            100                 105                 110

Asp Leu Lys Arg Gln Lys Glu Gln Ala Leu Arg Glu Val Glu His Leu
        115                 120                 125

Lys Arg Cys Gln Gln Gln Met Ala Glu Asp Lys Ala Ser Val Lys Ala
    130                 135                 140

Gln Val Thr Ser Leu Leu Gly Glu Leu Gln Glu Ser Gln Ser Arg Leu
145                 150                 155                 160

Glu Ala Ala Thr Lys Glu Cys Gln Ala Leu Glu Gly Arg Ala Arg Ala
                165                 170                 175

Ala Ser Glu Gln Ala Arg Gln Leu Glu Ser Arg Glu Ala Leu Gln
            180                 185                 190

Gln Gln His Ser Val Gln Val Asp Gln Leu Arg Met Gln Gly Gln Ser
        195                 200                 205

Val Glu Ala Ala Leu Arg Met Glu Arg Gln Ala Ala Ser Glu Glu Lys
    210                 215                 220

Arg Lys Leu Ala Gln Leu Gln Val Ala Tyr His Gln Leu Phe Gln Glu
225                 230                 235                 240
```

-continued

```
Tyr Asp Asn His Ile Lys Ser Ser Val Val Gly Ser Glu Arg Lys Arg
                245                 250                 255
Gly Met Gln Leu Glu Asp Leu Lys Gln Gln Leu Gln Gln Ala Glu Glu
            260                 265                 270
Ala Leu Val Ala Lys Gln Glu Val Ile Asp Lys Leu Lys Glu Glu Ala
        275                 280                 285
Glu Gln His Lys Ile Val Met Glu Thr Val Pro Val Leu Lys Ala Gln
    290                 295                 300
Ala Asp Ile Tyr Lys Ala Asp Phe Gln Ala Glu Arg Gln Ala Arg Glu
305                 310                 315                 320
Lys Leu Ala Glu Lys Lys Glu Leu Leu Gln Glu Gln Leu Glu Gln Leu
                325                 330                 335
Gln Arg Glu Tyr Ser Lys Leu Lys Ala Ser Cys Gln Glu Ser Ala Arg
            340                 345                 350
Ile Glu Asp Met Arg Lys Arg His Val Glu Val Ser Gln Ala Pro Leu
        355                 360                 365
Pro Pro Ala Pro Ala Tyr Leu Ser Ser Pro Leu Ala Leu Pro Ser Gln
    370                 375                 380
Arg Arg Ser Pro Pro Glu Glu Pro Pro Asp Phe Cys Cys Pro Lys Cys
385                 390                 395                 400
Gln Tyr Gln Ala Pro Asp Met Asp Thr Leu Gln Ile His Val Met Glu
                405                 410                 415
Cys Ile Glu

<210> SEQ ID NO 3
<211> LENGTH: 10
<212> TYPE: PRT
<213> ORGANISM: Homo sapiens

<400> SEQUENCE: 3

Ile Val Met Glu Thr Val Pro Val Leu Lys
1               5                   10

<210> SEQ ID NO 4
<211> LENGTH: 17
<212> TYPE: PRT
<213> ORGANISM: Homo sapiens

<400> SEQUENCE: 4

Lys Glu Leu Leu Gln Glu Gln Leu Glu Gln Leu Gln Arg Glu Tyr Ser
1               5                   10                  15
Lys

<210> SEQ ID NO 5
<211> LENGTH: 16
<212> TYPE: PRT
<213> ORGANISM: Homo sapiens

<400> SEQUENCE: 5

Glu Leu Leu Gln Glu Gln Leu Glu Gln Leu Gln Arg Glu Tyr Ser Lys
1               5                   10                  15

<210> SEQ ID NO 6
<211> LENGTH: 20
<212> TYPE: PRT
<213> ORGANISM: Homo sapiens

<400> SEQUENCE: 6
```

```
Arg His Val Glu Val Ser Gln Ala Pro Leu Pro Pro Ala Pro Ala Tyr
  1               5                  10                  15

Leu Ser Ser Pro
            20

<210> SEQ ID NO 7
<211> LENGTH: 20
<212> TYPE: PRT
<213> ORGANISM: Homo sapiens

<400> SEQUENCE: 7

Leu Ala Gln Leu Gln Val Ala Tyr His Gln Leu Phe Gln Glu Tyr Asp
  1               5                  10                  15

Asn His Ile Lys
            20

<210> SEQ ID NO 8
<211> LENGTH: 11
<212> TYPE: PRT
<213> ORGANISM: Homo sapiens
<220> FEATURE:
<221> NAME/KEY: UNSURE
<222> LOCATION: (1)

<400> SEQUENCE: 8

Xaa Gln Tyr Gln Ala Pro Asp Met Asp Thr Leu
  1               5                  10

<210> SEQ ID NO 9
<211> LENGTH: 17
<212> TYPE: PRT
<213> ORGANISM: Homo sapiens
<220> FEATURE:
<221> NAME/KEY: UNSURE
<222> LOCATION: (1)

<400> SEQUENCE: 9

Xaa Gln Pro Ser Gly Gly Pro Ala Ala Asp Gln Asp Val Leu Gly Glu
  1               5                  10                  15

Glu

<210> SEQ ID NO 10
<211> LENGTH: 13
<212> TYPE: PRT
<213> ORGANISM: Homo sapiens

<400> SEQUENCE: 10

Gln Gln Leu Gln Gln Ala Glu Glu Ala Leu Val Ala Lys
  1               5                  10

<210> SEQ ID NO 11
<211> LENGTH: 11
<212> TYPE: PRT
<213> ORGANISM: Homo sapiens

<400> SEQUENCE: 11

Glu Gln Ala Leu Arg Glu Val Glu His Leu Lys
  1               5                  10

<210> SEQ ID NO 12
<211> LENGTH: 9
<212> TYPE: PRT
<213> ORGANISM: Homo sapiens

<400> SEQUENCE: 12
```

-continued

```
Leu Val Glu Arg Leu Gly Leu Glu Lys
  1               5

<210> SEQ ID NO 13
<211> LENGTH: 15
<212> TYPE: PRT
<213> ORGANISM: Homo sapiens

<400> SEQUENCE: 13

Lys Glu Leu Leu Gln Glu Gln Leu Glu Gln Leu Gln Arg Glu Tyr
  1               5                  10                  15

<210> SEQ ID NO 14
<211> LENGTH: 14
<212> TYPE: PRT
<213> ORGANISM: Homo sapiens
<220> FEATURE:
<221> NAME/KEY: UNSURE
<222> LOCATION: (1)..(2)

<400> SEQUENCE: 14

Xaa Xaa Val Thr Ser Leu Leu Gly Glu Leu Gln Glu Ser Gln
  1               5                  10

<210> SEQ ID NO 15
<211> LENGTH: 13
<212> TYPE: PRT
<213> ORGANISM: Homo sapiens
<220> FEATURE:
<221> NAME/KEY: UNSURE
<222> LOCATION: (1)..(2)

<400> SEQUENCE: 15

Xaa Xaa Leu Gln Gln Ala Glu Glu Ala Leu Val Ala Lys
  1               5                  10

<210> SEQ ID NO 16
<211> LENGTH: 15
<212> TYPE: PRT
<213> ORGANISM: Homo sapiens
<220> FEATURE:
<221> NAME/KEY: UNSURE
<222> LOCATION: (1)
<220> FEATURE:
<221> NAME/KEY: UNSURE
<222> LOCATION: (5)
<220> FEATURE:
<221> NAME/KEY: UNSURE
<222> LOCATION: (8)
<220> FEATURE:
<221> NAME/KEY: UNSURE
<222> LOCATION: (13)

<400> SEQUENCE: 16

Xaa Gln Val Thr Xaa Leu Leu Xaa Glu Leu Gln Glu Xaa Gln Gln
  1               5                  10                  15

<210> SEQ ID NO 17
<211> LENGTH: 20
<212> TYPE: PRT
<213> ORGANISM: Homo sapiens
<220> FEATURE:
<221> NAME/KEY: UNSURE
<222> LOCATION: (1)

<400> SEQUENCE: 17

Xaa Ala Gln Leu Gln Val Ala Tyr His Gln Leu Phe Gln Glu Tyr Asp
  1               5                  10                  15
```

```
<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 18
agttgagggg actttcccag gc                                              22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 19
ttggattgaa gccaatatga ta                                              22
```

Asn His Ile Lys
        20